United States Patent
Bahnck et al.

(10) Patent No.: US 9,738,626 B2
(45) Date of Patent: Aug. 22, 2017

(54) ANTAGONISTS OF PROSTAGLANDIN EP3 RECEPTOR

(71) Applicant: Pfizer Inc., New York, NY (US)

(72) Inventors: Kevin Bahnck, Bridport, VT (US); Daniel Canterbury, Groton, CT (US); David James Edmonds, Arlington, MA (US); Kentaro Futatsugi, Quincy, MA (US); Esther Cheng Yin Lee, Brookline, MA (US); Elnaz Menhaji-Klotz, Somerville, MA (US); Jana Polivkova, Mystic, CT (US); Robert Vernon Stanton, Belmont, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/970,930

(22) Filed: Dec. 16, 2015

(65) Prior Publication Data

US 2016/0176851 A1 Jun. 23, 2016

Related U.S. Application Data

(60) Provisional application No. 62/095,337, filed on Dec. 22, 2014, provisional application No. 62/259,528, filed on Nov. 24, 2015.

(51) Int. Cl.
*C07D 401/14* (2006.01)
(52) U.S. Cl.
CPC .................. *C07D 401/14* (2013.01)
(58) Field of Classification Search
CPC .................................................. C07D 401/14
See application file for complete search history.

(56) References Cited

U.S. PATENT DOCUMENTS

| 4,219,483 A | 8/1980 | Kuhla et al. |
| 2008/0280877 A1 | 11/2008 | Dack et al. |
| 2015/0099782 A1 | 4/2015 | Bahnck et al. |

FOREIGN PATENT DOCUMENTS

| WO | 2006021418 | 3/2006 |
| WO | 2007027630 | 3/2007 |

OTHER PUBLICATIONS

Heptinstall, Platelets, Dec. 2008, vol. 19(8), 605-613.*
Flesch, et al., Novel prostaglandin receptor modulators—Part II: EP receptor modulators, a patent review (2002-2012), Expert Opinion on Therapeutic Patents, vol. 23(2), pp. 233-267 (2013).
Jin et al., "Novel 3-Oxazolidinedione-6-arylpyridinones as Potent, Selective, and Orally Active EP3 Receptor Antagonists", ACS Medicinal Chemistry Letters, vol. 1, pp. 316-320 (2010).
Kimple et al., "Prostaglandin E2 Receptor, EP3, Is Induced in Diabetic Islets and Negatively Regulates Glucose- and Hormone-Stimulated Insulin Secretion", Diabetes, vol. 62, pp. 1904-1912 (Jun. 2013).
Morales-Ramos et al., "Structure-activity relationship studies of novel 3-oxazolidinedione-6-naphthyl-2-pyridinones as potent and orally bioavailable EP3 receptor antagonists", Bioorganic & Medicinal Chemistry Letters, vol. 21, pp. 2806-2811 (2011).

* cited by examiner

*Primary Examiner* — D M Seaman
(74) *Attorney, Agent, or Firm* — Mary J. Hosley

(57) ABSTRACT

Provided herein are antagonists of prostaglandin EP3 receptor, processes to make said antagonists, and methods comprising administering said antagonists to a mammal in need thereof.

16 Claims, 2 Drawing Sheets

X-ray crystallographic structure showing the absolute configuration of (S)-3-(6-chloro-2-methoxypyridin-3-yl)-3-methylpiperidin-2-one.

X-ray crystallography of (R)-3-(2-methoxy-6-(1-methyl-1H-indol-5-yl)pyridin-3-yl)-3-methylpyrrolidin-2-one.

PXRD pattern of crystalline monohydrate form of Example 1

PXRD pattern of crystalline hydrochloride salt of Example 1

ANTAGONISTS OF PROSTAGLANDIN EP3 RECEPTOR

BACKGROUND OF THE INVENTION

Diabetes is a major public health concern because of its increasing prevalence and associated health risks. The disease is characterized by high levels of blood glucose resulting from defects in insulin production, insulin action, or both. Two major forms of diabetes are recognized, type I and type II. Type I diabetes develops when the body's immune system destroys pancreatic beta cells, the only cells in the body that make the hormone insulin that regulates blood glucose. To survive, people with type I diabetes must have insulin delivered by injection or a pump. Type II diabetes (T2D) accounts for about 90 to 95 percent of all diagnosed cases of diabetes. Type II diabetes usually begins as insulin resistance, a disorder in which the cells do not use insulin properly. Key target tissues, including liver, muscle, and adipose tissue, are resistant to the effects of insulin in stimulating glucose and lipid metabolism. As the need for insulin rises, the pancreas gradually loses its ability to produce insulin. Controlling type II diabetes with medication is essential; otherwise, it can progress into pancreatic beta-cell failure requiring complete dependence on insulin.

Several drugs in five major categories, each acting by different mechanisms, are available for treating hyperglycemia and subsequently, T2D (Moller, D. E., "New drug targets for Type II diabetes and the metabolic syndrome" Nature 414; 821-827, (2001)): (A) Insulin secretogogues, including sulphonyl-ureas (e.g., glipizide, glimepiride, glyburide) and meglitinides (e.g., nateglidine and repaglinide), dipeptidyl peptidase IV (DPP-IV) inhibitors (e.g., those in WO2005116014, sitagliptin, vildagliptin, alogliptin, dutogliptin, linagliptin, and saxogliptin), and glucagon-like peptide 1 (GLP-1) agonists (e.g, liraglutide, albiglutide, exenatide (Byetta®), albiglutide, lixisenatide, dulaglutide, semaglutide) enhance secretion of insulin by acting on the pancreatic beta-cells. (B) Biguanides (e.g., metformin) are thought to act primarily by decreasing hepatic glucose production. Biguanides often cause gastrointestinal disturbances and lactic acidosis, further limiting their use. (C) Inhibitors of alpha-glucosidase (e.g., acarbose) decrease intestinal glucose absorption. These agents often cause gastrointestinal disturbances. (D) Thiazolidinediones (e.g., pioglitazone, rosiglitazone) act on a specific receptor (peroxisome proliferator-activated receptor-gamma) in the liver, muscle and fat tissues. They regulate lipid metabolism subsequently enhancing the response of these tissues to the actions of insulin. Frequent use of these drugs may lead to weight gain and may induce edema and anemia. (E) Insulin is used in more severe cases, either alone or in combination with the above agents.

Ideally, an effective new treatment for T2D would meet the following criteria: (a) it would not have significant side effects including induction of hypoglycemia; (b) it would not cause weight gain; (c) it would at least partially replace insulin by acting via mechanism(s) that either increase endogenous insulin secretion or are independent from the actions of insulin; (d) it would desirably be metabolically stable to allow less frequent usage; and (e) it would be usable in combination with tolerable amounts of any of the categories of drugs listed herein. There continues to be a need for new effective treatments for T2D.

SUMMARY OF THE INVENTION

The present invention concerns compounds of Formula I that include tautomers of compounds of Formula Ia and Formula Ib:

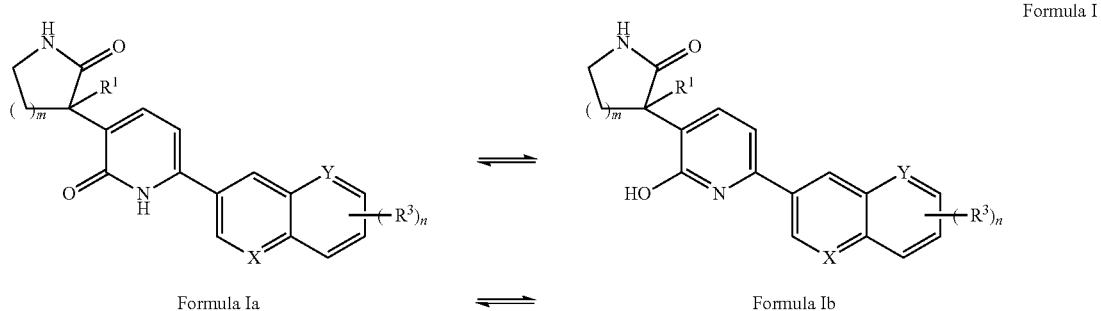

Formula I

Formula Ia ⇌ Formula Ib

The compounds of the present invention may generally be drawn as compounds of either Formula Ia or Formula Ib, but general reference to compounds of Formula I is to be understood that this representation includes both tautomers of compounds of Formula Ia and Formula Ib. However, reference to one tautomer is intended to include that one tautomer, e.g., compounds of Formula Ia, or pharmaceutically acceptable salts thereof, or, independently, compounds of Formula Ib, or pharmaceutically acceptable salts thereof.

The present invention concerns a compound of Formula I:

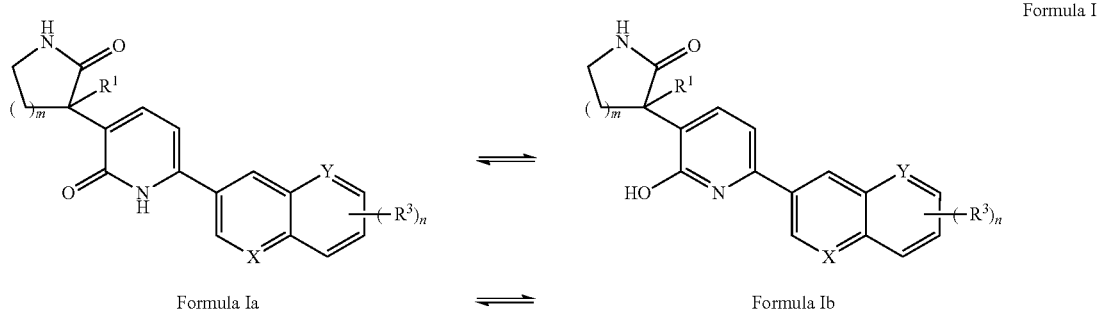

Formula I

Formula Ia ⇌ Formula Ib wherein m is 1 or 2;
n is 0, 1, or 2;
X and Y are nitrogen or $CR^2$, provided that when X is nitrogen, Y is $CR^2$ and further provided that when X is $CR^2$, Y is nitrogen;
$R^1$ is H, $C_{1-6}$alkyl, or $C_{3-6}$cycloalkyl;
$R^2$ is H, halogen, $C_{1-6}$alkyl, or $C_{3-6}$cycloalkyl, wherein alkyl may be substituted with up to 3 halogens; and
Each $R^3$ is independently halogen, $C_{1-6}$alkyl, or $C_{3-6}$cycloalkyl, wherein alkyl may be substituted with up to 3 halogens;
or a pharmaceutically acceptable salt thereof, or a solvate of said compound or salt thereof.

Another embodiment of the invention concerns a compound of Formula I, or a pharmaceutically acceptable salt thereof, as defined in any of the embodiments described herein, for use in the treatment of any one or more of bladder over activity, cerebrovascular disease, coronary artery disease, peripheral vascular disease, hypertension, congestive heart failure, myocardial infarction, stroke, hemorrhagic stroke, ischemic stroke, pulmonary hypertension, neurodegenerative disorders, pain, premature labor, restinosis, thrombosis, Type I diabetes, and/or Type II diabetes.

DETAILED DESCRIPTION OF THE INVENTION

Figure 1:
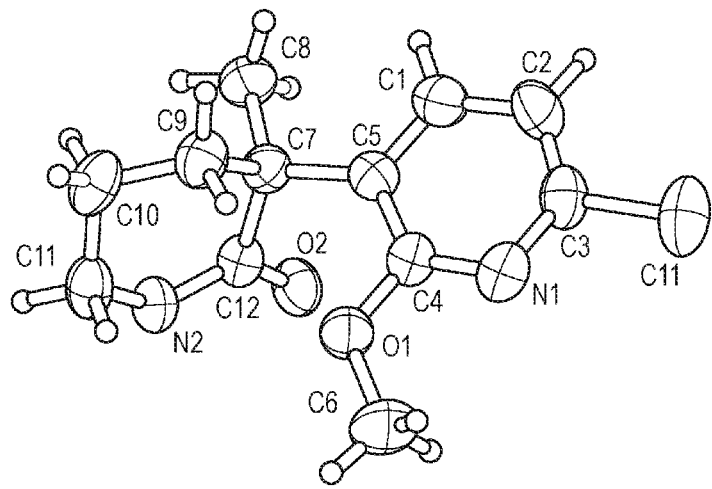
FIG. 1 is a X-ray crystal structure (ORTEP drawing) of (S)-3-(6-chloro-2-methoxypyridin-3-yl)-3-methylpiperidin-2-one.

The present invention may be understood more readily by reference to the following detailed description of exemplary embodiments of the invention and the examples included therein.

Another embodiment of the invention concerns compounds of Formula I, wherein
m is 1 or 2;
n is 0, 1, or 2;
X is nitrogen;
Y is $CR^2$;
$R^1$ is H, $C_{1-6}$alkyl, or $C_{3-6}$cycloalkyl;
$R^2$ is F, Cl, $C_{1-3}$alkyl or cyclopropyl, wherein alkyl may be substituted with up to 3 halogens; and
Each $R^3$ is independently halogen, $C_{1-6}$alkyl, or $C_{3-6}$cycloalkyl, wherein alkyl may be substituted with up to 3 halogens; or a pharmaceutically acceptable salt thereof, or a solvate of said compound or salt thereof.

Another embodiment of the invention concerns compounds of Formula I, wherein
m is 1 or 2;
n is 0, 1, or 2;
Y is nitrogen;
X is $CR^2$;
$R^1$ is H, $C_{1-6}$alkyl, or $C_{3-6}$cycloalkyl;
$R^2$ is F, Cl, $C_{1-3}$alkyl or cyclopropyl, wherein alkyl may be substituted with up to 3 halogens; and
Each $R^3$ is independently halogen, $C_{1-6}$alkyl, or $C_{3-6}$cycloalkyl, wherein alkyl may be substituted with up to 3 halogens; or a pharmaceutically acceptable salt thereof, or a solvate of said compound or salt thereof.

Another embodiment of the invention concerns compounds of Formula I, wherein
m is 1 or 2;
n is 0;
X is nitrogen;
Y is $CR^2$;
$R^1$ is H, $C_{1-3}$alkyl, or cyclopropyl; and
$R^2$ is F, Cl, $C_{1-3}$alkyl or cyclopropyl, wherein alkyl may be substituted with up to 3 halogens; or a pharmaceutically acceptable salt thereof, or a solvate of said compound or salt thereof.

Another embodiment of the invention concerns compounds of Formula I, wherein
m is 1 or 2;
n is 0;
Y is nitrogen;
X is $CR^2$;
$R^1$ is H, $C_{1-3}$alkyl, or cyclopropyl; and
$R^2$ is F, Cl, $C_{1-3}$alkyl or cyclopropyl, wherein alkyl may be substituted with up to 3 halogens; or a pharmaceutically acceptable salt thereof, or a solvate of said compound or salt thereof.

Another embodiment of the invention concerns compounds of Formula I as described herein, wherein X, Y, $R^2$, and $R^3$ provide

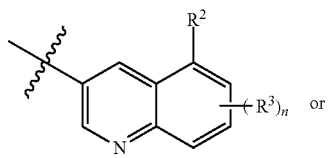

or

-continued

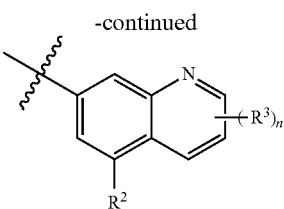

n is 0 or 1;

R² is F, Cl, methyl, ethyl, CFH₂, CF₂H, CF₂CH₃, CF₃, or cyclopropyl; and

R³ is F, Cl, methyl, ethyl, CFH₂, CF₂H, CF₂CH₃, CF₃, or cyclopropyl; or a pharmaceutically acceptable salt thereof, or a solvate of said compound or salt thereof.

In embodiments where R³ is present, each R³ may substitute any carbon of the six-membered ring identified with an *:

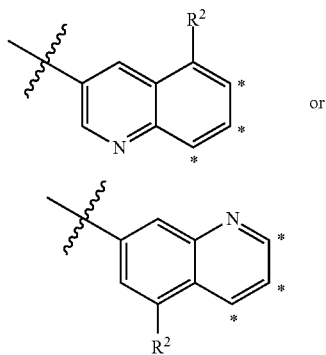

Another embodiment of the invention concerns compounds of Formula I as described herein, wherein X, Y, and R² provide

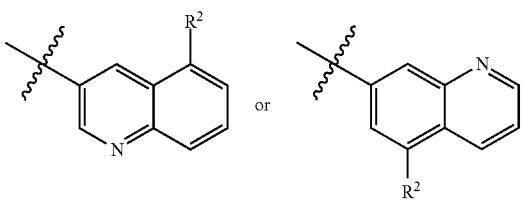

n is 0; and

R² is F, Cl, methyl, ethyl, CFH₂, CF₂H, CF₂CH₃, CF₃, or cyclopropyl; or a pharmaceutically acceptable salt thereof, or a solvate of said compound or salt thereof.

Another embodiment of the invention concerns compounds of Formula I as described herein, wherein X, Y, and R² provide

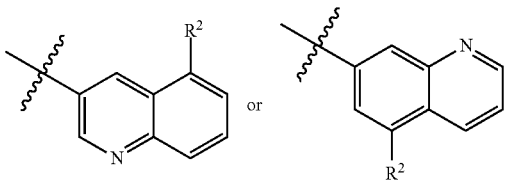

n is 0; and

R² is F, Cl, methyl, ethyl, or cyclopropyl; or a pharmaceutically acceptable salt thereof, or a solvate of said compound or salt thereof.

For ease of reference, when n is 0, R³ is not shown in Formula I.

Another embodiment of the invention concerns compounds of Formula I as described herein, wherein m is 1, or a pharmaceutically acceptable salt thereof, or a solvate of said compound or salt thereof.

Another embodiment of the invention concerns compounds of Formula I as described herein, wherein m is 2, or a pharmaceutically acceptable salt thereof, or a solvate of said compound or salt thereof.

Another embodiment of the invention concerns compounds of Formula I as described herein, wherein R¹ is CH₃, or a pharmaceutically acceptable salt thereof, or a solvate of said compound or salt thereof.

The embodiments discussed herein may include a solvate of the compound of Formula I or a solvate of a pharmaceutically acceptable salt thereof. By way of example and not limitation, an embodiment of the invention concerns the compound of Formula I, wherein the compound is (R)-3-(3-Methyl-2-oxopiperidin-3-yl)-6-(5-methylquinolin-3-yl)pyridin-2(1H)-one or (R)-3-(2-hydroxy-6-(5-methylquinolin-3-yl)pyridin-3-yl)-3-methylpiperidin-2-one, or mixtures thereof, or a pharmaceutically acceptable salt thereof, or a solvate of said compound or salt thereof. Yet another embodiment of the invention concerns the compound of Formula I, wherein the compound is (R)-3-(3-Methyl-2-oxopiperidin-3-yl)-6-(5-methylquinolin-3-yl)pyridin-2(1H)-one or (R)-3-(2-hydroxy-6-(5-methylquinolin-3-yl)pyridin-3-yl)-3-methylpiperidin-2-one, or mixtures thereof, or a pharmaceutically acceptable salt thereof. Yet another embodiment of the invention concerns the compound of Formula I, wherein the compound is (R)-3-(3-Methyl-2-oxopiperidin-3-yl)-6-(5-methylquinolin-3-yl)pyridin-2(1H)-one or a pharmaceutically acceptable salt thereof, or a solvate of said compound or salt thereof. Yet another embodiment of the invention concerns the compound of Formula I, wherein the compound is (R)-3-(3-Methyl-2-oxopiperidin-3-yl)-6-(5-methylquinolin-3-yl)pyridin-2(1H)-one, or a pharmaceutically acceptable salt thereof. Yet another embodiment of the invention concerns the compound of Formula I, wherein the compound is (R)-3-(2-hydroxy-6-(5-methylquinolin-3-yl)pyridin-3-yl)-3-methylpiperidin-2-one, or a pharmaceutically acceptable salt thereof, or a solvate of said compound or salt thereof. Yet another embodiment of the invention concerns the compound of Formula I, wherein the compound is (R)-3-(2-hydroxy-6-(5-methylquinolin-3-yl)pyridin-3-yl)-3-methylpiperidin-2-one, or a pharmaceutically acceptable salt thereof.

Compounds of Formula I are tautomers between pyridinones and hydroxyl pyridines, but for ease of reference, will be referred to generally as substituted pyridinones. Reference to a compound of Formula I in embodiments discussed herein includes a pharmaceutically acceptable salt or a solvate of the compound of Formula I or a solvate of a pharmaceutically acceptable salt thereof. The invention may be understood more readily by reference to the following detailed description of exemplary embodiments of the invention and the examples presented herein. It is to be understood that this invention is not limited to specific synthetic methods of making that may of course vary. It is also to be understood that the terminology used herein is for the purpose of describing particular embodiments only and is not intended to be limiting.

As used herein, a wavy line,

denotes a point of attachment of a substituent to another group.

As used throughout this specification and the appended claims, the following terms have the following meanings:

The term "$C_{1-6}$alkyl" as used herein, means a straight or branched chain hydrocarbon containing from 1 to 6 carbon atoms. Non-limiting examples of ($C_{1-6}$)alkyl include methyl, ethyl, n-propyl, iso-propyl, n-butyl, sec-butyl, iso-butyl, tert-butyl, n-pentyl, isopentyl, neopentyl, and n-hexyl.

The term "$C_{1-3}$alkyl" as used herein, means a straight or branched chain hydrocarbon containing from 1 to 3 carbon atoms. Non-limiting examples of ($C_{1-3}$)alkyl include methyl, ethyl, n-propyl, and iso-propyl.

The term "$C_{3-6}$cycloalkyl" as used herein, means a cyclic alkyl moiety containing from 3 to 6 carbon atoms. Non-limiting examples of ($C_{3-6}$)cycloalkyl include cyclopropyl, cyclobutyl, cyclopentyl, and cyclohexyl.

The term "halogen" as used herein means chloro (Cl), fluoro (F), bromo (Br), or iodo (I).

The invention relates to a compound of Formula I, or a pharmaceutically acceptable salt thereof, used as an EP3 receptor antagonist.

The invention also relates to a compound of Formula I, or a pharmaceutically acceptable salt thereof, used as an EP3 receptor antagonist that may be used in the treatment of any one or more of the following: bladder overactivity, cerebrovascular disease, coronary artery disease, peripheral vascular disease, hypertension, neurodegenerative disorders, pain, premature labor, restinosis, thrombosis, Type I diabetes, and/or Type II diabetes.

The invention also relates to (1) a compound of Formula I, or a pharmaceutically acceptable salt thereof, as defined in any of the embodiments described above, for use as a medicament; and (2) a compound of Formula I, or a pharmaceutically acceptable salt thereof, as defined in any of the embodiments described herein, for use in the treatment of any one or more of bladder overactivity, cerebrovascular disease, coronary artery disease, peripheral vascular disease, hypertension, congestive heart failure, myocardial infarction, stroke, hemorrhagic stroke, ischemic stroke, pulmonary hypertension, neurodegenerative disorders, pain, premature labor, restinosis, thrombosis, Type I diabetes, and/or Type II diabetes.

The present invention also provides any one or combination of:

a method of treating a disease for which an antagonist of EP3 is indicated, in a subject in need of such treatment, comprising administering to the subject a therapeutically effective amount of a compound of Formula I, or a pharmaceutically acceptable salt thereof;

the use of a compound of Formula I, or a pharmaceutically acceptable salt thereof, for the manufacture of a medicament for treating a disease or condition for which an antagonist of EP3 is indicated;

a compound of Formula I, or a pharmaceutically acceptable salt thereof, for use as a medicament;

a compound of Formula I, or a pharmaceutically acceptable salt thereof, for use in the treatment of a disease or condition for which an antagonist of EP3 is indicated;

a pharmaceutical composition comprising a compound of Formula I, or a pharmaceutically acceptable salt thereof, and a pharmaceutically acceptable excipient;

a pharmaceutical composition for the treatment of a disease or condition for which an antagonist of EP3 is indicated, comprising a compound of Formula I, or a pharmaceutically acceptable salt thereof.

The invention also relates to a pharmaceutical composition comprising a compound of Formula I, or a pharmaceutically acceptable salt thereof, as defined in any of the embodiments described herein, for use in the treatment of any one or more of the following: bladder overactivity, cerebrovascular disease, coronary artery disease, hypertension, peripheral vascular disease, neurodegenerative disorders, pain, premature labor, restinosis, thrombosis, Type I diabetes, and/or Type II diabetes.

Another embodiment of the invention concerns a compound of Formula I, or a pharmaceutically acceptable salt thereof, as defined in any of the embodiments described herein, for use in the treatment of any one or more of bladder over activity, cerebrovascular disease, coronary artery disease, peripheral vascular disease, hypertension, congestive heart failure, myocardial infarction, stroke, hemorrhagic stroke, ischemic stroke, pulmonary hypertension, neurodegenerative disorders, pain, premature labor, restinosis, thrombosis, Type I diabetes, and/or Type II diabetes.

In another embodiment, the invention provides a pharmaceutical composition comprising a compound of Formula I, or a pharmaceutically acceptable salt thereof, as defined in any of the embodiments described herein, in admixture with at least one pharmaceutically acceptable excipient.

In another embodiment, the invention provides a pharmaceutical composition comprising a compound of Formula I, or a pharmaceutically acceptable salt thereof, as defined in any of the embodiments described herein, in admixture with at least one other therapeutic agent described herein.

Another embodiment of the present invention concerns all embodiments herein, wherein the compounds of Formula I are compounds of Formula Ia, or a pharmaceutically acceptable salt thereof.

Another embodiment of the present invention concerns all embodiments herein, wherein the compounds of Formula I are compounds of Formula Ib, or a pharmaceutically acceptable salt thereof.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" refers to warm blooded animals, including humans (male or female) and companion animals (e.g., dogs, cats, horses, etc.), and other animals including guinea pigs, mice, rats, gerbils, cattle, goats, sheep, monkeys, and chimpanzees.

The term "patient" is an alternative reference for mammal.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment, i.e., relieve, alleviate, or slow the progression of the patient's disease (or condition) or any tissue damage associated with the disease.

The term "antagonist" includes both full antagonists and partial antagonists, as well as inverse agonists.

As used herein, the term "Formula I" may be referred to as a "compound(s) of the invention," "the invention," and "compound of Formula I." Such terms are used interchangeably. Such terms are also defined to include all forms of the compound of Formula I, including hydrates, solvates, clathrates, isomers, crystalline (including co-crystals) and non-crystalline forms, isomorphs, polymorphs, tautomers, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the present invention may contain asymmetric or chiral centers, and, therefore, exist in different stereoisomeric forms. Unless specified otherwise, it is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereoisomers and converting (e.g. hydrolyzing) the individual diastereoisomers to the corresponding pure enantiomers. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation.

Where the compounds of the present invention possess two or more stereogenic centers and the absolute or relative stereochemistry is given in the name, the designations R and S refer respectively to each stereogenic center in ascending numerical order (1, 2, 3, etc.) according to the conventional IUPAC number schemes for each molecule. Where the compounds of the present invention possess one or more stereogenic centers and no stereochemistry is given in the name or structure, it is understood that the name or structure is intended to encompass all forms of the compound, including the racemic form.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. For example, the following is illustrative of tautomers of the compounds of Formula I.

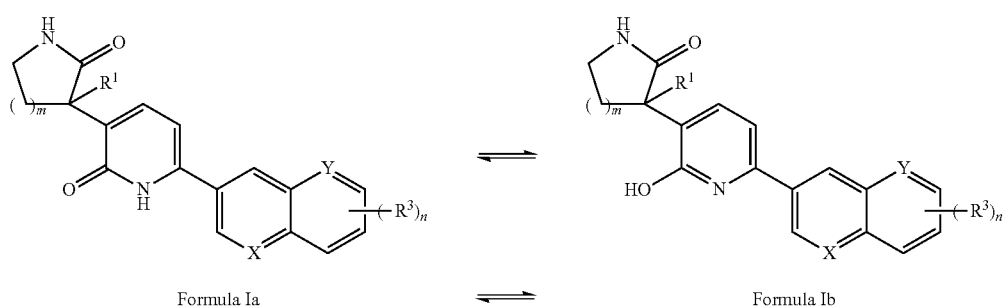

Formula I

Formula Ia ⇌ Formula Ib

Valence tautomers include interconversions by reorganization of some of the bonding electrons.

Included within the scope of the claimed compounds of the present invention are all stereoisomers, geometric isomers and tautomeric forms of the compounds of Formula I, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

The present invention includes all pharmaceutically acceptable isotopically-labelled compounds of Formula I wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}$H and $^{3}$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O.

Certain isotopically-labelled compounds of Formula I, for example, those incorporating a radioactive isotope, are useful in drug and/or substrate tissue distribution studies. The radioactive isotopes tritium, i.e. $^{3}$H, and carbon-14, i.e. $^{14}$C, are particularly useful for this purpose in view of their ease of incorporation and ready means of detection.

Substitution with heavier isotopes such as deuterium, i.e. $^{2}$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Tomography (PET) studies for examining substrate receptor occupancy.

Isotopically-labelled compounds of Formula I can generally be prepared by conventional techniques known to those skilled in the art or by processes analogous to those described in the accompanying Examples and Preparations using an appropriate isotopically-labelled reagents in place of the non-labelled reagent previously employed.

The compounds of the present invention may be isolated and used per se, or when possible, in the form of its pharmaceutically acceptable salt. The term "salts" refers to inorganic and organic salts of a compound of the present invention. These salts can be prepared in situ during the final isolation and purification of a compound, or by separately treating the compound with a suitable organic or inorganic acid or base and isolating the salt thus formed. The acids which are used to prepare the pharmaceutically acceptable acid addition salts of the aforementioned base compounds of this invention are those which form non-toxic acid addition salts, (i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, naphthylate, mesylate, glucoheptonate, lactobionate, laurylsulphonate, hexafluorophosphate, benzene sulfonate, tosylate, formate, trifluoroacetate, oxalate, besylate, palmitiate, pamoate, malonate, stearate, laurate, malate, borate, p-toluenesulfonate and pamoate (i.e., 1,1'-methylene-bis-(2-hydroxy-3-naphthoate)) salts.

The invention also relates to base addition salts of the compounds of the present invention. The chemical bases that may be used as reagents to prepare pharmaceutically acceptable base salts of those compounds of the present invention that are acidic in nature are those that form non-toxic base salts with such compounds. Such non-toxic base salts include, but are not limited to those derived from such pharmacologically acceptable cations such as alkali metal cations (e.g., lithium, potassium and sodium) and alkaline earth metal cations (e.g., calcium and magnesium), ammonium or water-soluble amine addition salts such as N-methylglucamine-(meglumine), tetramethylammonium, tetraethylammonium, methylamine, dimethylamine, trimethylamine, triethylamine, ethylamine, and the lower alkanolammonium and other base salts of pharmaceutically acceptable organic amines. See e.g. Berge, et al. *J. Pharm. Sci.* 66, 1-19 (1977).

Certain compounds of the present invention may exist in more than one crystal form (generally referred to as "polymorphs"). Polymorphs may be prepared by crystallization under various conditions, for example, using different solvents or different solvent mixtures for recrystallization; crystallization at different temperatures; and/or various modes of cooling, ranging from very fast to very slow cooling during crystallization. Polymorphs may also be obtained by heating or melting the compound of the present invention followed by gradual or fast cooling. The presence of polymorphs may be determined by solid probe NMR spectroscopy, IR spectroscopy, differential scanning calorimetry, powder X-ray diffraction or such other techniques.

In another embodiment of the present invention, a compound of Formula I may be co-administered with an anti-obesity agent where the anti-obesity agent is selected from the group consisting of gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or U.S Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), $PYY_{3-36}$ (as used herein "$PYY_{3-36}$" includes analogs, such as peglated $PYY_{3-36}$ e.g., those described in U.S Publication 2006/0178501), opioid antagonists (e.g., naltrexone), the combination of naltrexone with buproprion, oleoyl-estrone (CAS No. 180003-17-2), obinepitide (TM30338), pramlintide (Symlin®), tesofensine (NS2330), leptin, liraglutide, bromocriptine, orlistat, exenatide (Byetta®), AOD-9604 (CAS No. 221231-10-3) and sibutramine.

Other anti-obesity agents include 11β-hydroxy steroid dehydrogenase-1 (11β-HSD type 1) inhibitors, stearoyl-CoA desaturase-1 (SCD-1) inhibitor, cholecystokinin-A (CCK-A) agonists, monoamine reuptake inhibitors (such as sibutramine), sympathomimetic agents, $β_3$ adrenergic agonists, dopamine agonists (such as bromocriptine), melanocyte-stimulating hormone analogs, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, the combination of naltrexone with buproprion and the like.

In another embodiment of the present invention, a compound of Formula I may be co-administered with an anti-diabetic agent, where the anti-diabetic agent is selected from the group consisting of an acetyl-CoA carboxylase- (ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3, exendin-4, ZYOG-1 and TTP273), liraglutide (Victoza®), albiglutide, exenatide (Byetta®, Bydureon®), albiglutide, lixisenatide, dulaglutide, semaglutide (NN-9924), TTP-054, a protein tyrosine phosphatase-1B (PTP-1B) inhibitor (e.g., trodusquemine, hyrtiosal extract, and compounds disclosed by Zhang, S., et al., *Drug Discovery Today,* 12(9/10), 373-381 (2007)), SIRT-1 activator (e.g., resveratrol, GSK2245840 or GSK184072), a dipeptidyl peptidease IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, empagliflozin, tofogliflozin (CSG452), ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4)359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235, listing of anti-diabetic agents found at page 28, line 35 through page 30, line 19 of WO2011005611, inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1 beta, modulators of RXRalpha, suitable anti-diabetic agents include mechanisms listed by Carpino, P. A., Goodwin, B. Expert Opin. Ther. Pat, 2010, 20(12), 1627-51.

Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1 beta, modulators of RXRalpha.

In another embodiment of the present invention, a compound of Formula I may be co-administered with a cholesterol/lipid modulating agent, where the cholesterol/lipid modulating agent is selected from the group consisting of HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); HMG-CoA reductase gene expression inhibitor; squalene synthetase inhibitors; a squalene epoxidase inhibitor; a squalene cyclase inhibitor; a combined squalene epoxidase/squalene cyclase inhibitor a CETP inhibitor; fibrates; niacin, an ion-exchange resin, an antioxidant; bile acid sequestrants (such as questran); ACAT inhibitors; MTP/APO β secretion inhibitors; lipooxygenase inhibitors; cholesterol absorption inhibitors; cholesteryl ester transfer protein inhibitors; an agent such as mipomersen; and or atherosclerotic agents including PCSK9 modulators.

In another embodiment, a compound of Formula I may be co-administered with agents for the treatment of non-alcoholic steatohepatitis (NASH) and/or non-alcoholic fatty liver disease (NAFLD), such as Orlistat, TZDs and other insulin sensitizing agents, FGF21 analogs, Metformin, Omega-3-acid ethyl esters (e.g. Lovaza), Fibrates, HMG CoA-reductase Inhibitors, Ezitimbe, Probucol, Ursodeoxycholic acid, TGR5 agonists, FXR agonists, Vitamin E, Betaine, Pentoxifylline, CB1 antagonists, Carnitine, N-acetylcysteine, Reduced glutathione, lorcaserin, the combination of naltrexone with buproprion, SGLT2 Inhibitors, Phentermine, Topiramate, Incretin (GLP and GIP) analogs and Angiotensin-receptor blockers.

Additional therapeutic agents include anti-coagulant or coagulation inhibitory agents, anti-platelet or platelet inhibitory agents, thrombin inhibitors, thrombolytic or fibrinolytic agents, anti-arrythmic agents, anti-hypertensive agents, calcium channel blockers (L-type and T-type), cardiac glycosides, diruetics, mineralocorticoid receptor antagonists, NO donating agents such as organonitrates, NO promoting agents such as phosphodiesterase inhibitors, Soluble Guanylate Cyclase (sGC) modulators which include stimulators (e.g. Riociguat, Vericiguat etc.) or activators (e.g. cinaciguat, ataciguat), cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid hormone receptor antagonist), anti-infective agents, anti-viral agents, anti-bacterial agents, and anti-fungal agents.

Agents used in an ICU setting are included, for example, dobutamine, dopamine, dpinephrine, nitroglycerin, nitroprusside etc.

Combination agents useful for treating vasculitis are included, for example, azathioprine, cyclophosphamide, mycophenolate, mofetil, rituximab etc.

In another embodiment, the present invention provides a combination wherein the second agent is at least one agent selected from a factor Xa inhibitor, an anti-coagulant agent, an anti-platelet agent, a thrombin inhibiting agent, a thrombolytic agent, and a fibrinolytic agent. Exemplary factor Xa inhibitors include apixaban and rivaroxaban. Examples of suitable anti-coagulants for use in combination with the compounds of the present invention include heparins (e.g., unfractioned and low molecular weight heparins such as enoxaparin and dalteparin).

In another preferred embodiment the second agent is at least one agent selected from warfarin, dabigatran, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

A preferred second agent is at least one anti-platelet agent. Especially preferred anti-platelet agents are aspirin and clopidogrel.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and COX-2 inhibitors such as CELEBREX or piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., Pletal, dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticagrelor, prasugrel, ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, dabigatran, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents include: Class I agents (such as propafenone); Class II agents (such as metoprolol, atenolol, carvadiol and propranolol); Class III agents (such as sotalol, dofetilide, amiodarone, azimilide and ibutilide); Class IV agents (such as ditiazem and verapamil); $K^+$ channel openers such as $I_{Ach}$ inhibitors, and $I_{Kur}$ inhibitors (e.g., compounds such as those disclosed in WO01/40231).

The compounds of the present invention may be used in combination with antihypertensive agents and such antihypertensive activity is readily determined by those skilled in the art according to standard assays (e.g., blood pressure measurements). Examples of suitable anti-hypertensive agents include: alpha adrenergic blockers; beta adrenergic blockers; calcium channel blockers (e.g., diltiazem, verapamil, nifedipine and amlodipine); vasodilators (e.g., hydralazine), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, am iloride, spironolactone); relaxin receptor agonists (e.g Serelaxin); renin inhibitors; ACE inhibitors (e.g., captopril, zofenopril, fosinopril, enalapril, ceranopril, cilazopril, delapril, pentopril, quinapril, ram ipril, lisinopril); Angiotensin Receptor Blockers (ARBs), including specifically AT-1 receptor antagonists, (e.g., losartan, irbesartan, valsartan, azilsartan, candesartan, eprosartan, olmesartan, and telmisartan); ET receptor antagonists (e.g., sitaxsentan, atrsentan and compounds disclosed in U.S. Pat. Nos. 5,612,359 and 6,043,265); Dual ET/All antagonist (e.g., compounds disclosed in WO 00/01389); neutral endopeptidase (NEP) inhibitors; vasopepsidase inhibitors (dual NEP-ACE inhibitors) (e.g., gemopatrilat and nitrates). An exemplary antianginal agent is ivabradine.

Examples of suitable calcium channel blockers (L-type or T-type) include diltiazem, verapamil, nifedipine and amlodipine and mybefradil.

Examples of suitable cardiac glycosides include digitalis and ouabain.

In one embodiment, a Formula I compound may be co-administered with one or more neprilysin inhibitor (e.g., Sacubitril, Omapatrilat, RB-101 (or modifications thereof such as RB-120 and RB-3007), and UK-414,495).

In one embodiment, a Formula I compound may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™); (b) thiazide-type diuretics such as chlorothiazide (such as DIURIL™, ESIDRIX™ or HYDRODIURIL™) hydrochlorothiazide (such as MICROZIDE™ or ORETIC™), benzthiazide, hydroflumethiazide (such as SALURON™), bendroflumethiazide, methychlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™).

In another embodiment, a compound of Formula I may be co-administered with a loop diuretic. In still another embodiment, the loop diuretic is selected from furosemide and torsemide. In still another embodiment, one or more compounds of Formula I may be co-administered with furosemide. In still another embodiment, one or more compounds of Formula I may be co-administered with torsemide which may optionally be a controlled or modified release form of torsemide.

In another embodiment, a compound of Formula I may be co-administered with a thiazide-type diuretic. In still another embodiment, the thiazide-type diuretic is selected from the group consisting of chlorothiazide and hydrochlorothiazide. In still another embodiment, one or more compounds of Formula I may be co-administered with chlorothiazide. In still another embodiment, one or more compounds of Formula I may be co-administered with hydrochlorothiazide.

In another embodiment, one or more compounds of Formula I may be co-administered with a phthalimidine-type diuretic. In still another embodiment, the phthalimidine-type diuretic is chlorthalidone.

Examples of suitable mineralocorticoid receptor antagonists include sprionolactone and eplerenone.

Examples of suitable phosphodiesterase inhibitors include: PDE III inhibitors (such as cilostazol); PDE V inhibitors (such as sildenafil); PDE 9 inhibitors (such as BAY 73-6691 (Bayer AG); those in U.S Patent Publication Nos.US2003/0195205, US2004/0220186,US2006/0111372, and US2006/0106035; and those in U.S. Pat. No. 7,964,607) and PDE2 inhibitors (such BAY 60-7550, and those in WO2012/114222 and/or WO2012/168817).

Those skilled in the art will recognize that the compounds of this invention may also be used in conjunction with other cardiovascular or cerebrovascular treatments including PCI, stenting, drug eluting stents, stem cell therapy and medical devices such as implanted pacemakers, defibrillators, or cardiac resynchronization therapy.

In another embodiment, the disease and/or condition treated is selected from the group consisting of hyperlipidemia, Type I diabetes, Type II diabetes mellitus, idiopathic Type I diabetes (Type Ib), latent autoimmune diabetes in adults (LADA), early-onset Type II diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction (e.g. necrosis and apoptosis), dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, angina pectoris, thrombosis, atherosclerosis, myocardial infarction, transient ischemic attacks, stroke, vascular restenosis, hyperglycemia, hyperinsulinemia, hyperlipidemia, hypertrygliceridemia, insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance, hyper apo B lipoproteinemia, Alzheimer's, schizophrenia, impaired cognition, inflammatory bowel disease, ulcerative colitis, Crohn's disease, and irritable bowel syndrome, non-alcoholic steatohepatitis (NASH), non-alcoholic fatty liver disease (NAFLD).

Multiple studies have demonstrated that prostaglandin E2 (PGE2) inhibits glucose-stimulated insulin secretion (GSIS) in humans. Robertson R P and Chen M (1977) *J Clin Invest* 60 747-53; Konturek S J, et al. (1978) *Prostaglandins* 15 591-602; Giugliano D et al (1983) *Am J Physiol Endocrinol Metab* 245 E591-7. The inhibition of PGE2 production has also been shown to partially restore acute GSIS, adding strength to the hypothesis that increased local production of PGE2 is a contributor to defective insulin secretion observed in diabetic patients. See infra Robertson, et al.; Chen M and Robertson R P (1978) *Diabetes* 27 750-6; McRae J R, et al. (1981) *Metabolism* 30 1065-1075; Giugliano D, et al. (1985) *J Clin Endocrinol Metab* 61 160-6. Using theophylline to maintain increased intracellular cAMP, a subsequent study confirmed that this signaling molecule was a critical component of the inhibitory action of PGE2 on GSIS. Giugliano D, et al. (1988) *Acta Endocrinologica* (Copenh) 118, 187-192. Of the four distinct receptors for the PGE2 ligand (EP1-EP4), it is therefore EP3 which has the strongest rationale as the prostanoid receptor which mediates the inhibitory effect of PGE2 on GSIS. Legler D F, et al. (2010) *Int J Biochem Cell Biol* 42 198-201. The functional link from PGE2 suppression of GSIS through EP3 has recently been confirmed using animal models and cell lines. Kimple M E, et al. (2013) *Diabetes* 62 1904-12. When taken together, these observations indicate that EP3 receptor antagonists may be useful to relieve the inhibitory action of PGE2 in diabetic patients and at least partially restore defective GSIS.

In another embodiment, the invention provides a method of affecting insulin secretion, the method comprising the administration to a mammal in need thereof a therapeutically effect amount of an EP3 antagonist. The invention further provides a method of affecting insulin secretion, the method comprising the administration to a mammal in need thereof a therapeutically effect amount of an EP3 antagonist, where the EP3 antagonist is a compound of Formula I or pharmaceutically acceptable salt thereof.

In another embodiment, the invention provides a method of increasing insulin secretion in response to the presence of glucose, the method comprising the administration to a mammal in need thereof, a therapeutically effect amount of an EP3 antagonist. The invention further provides a method of improving insulin secretion, the method comprising the administration to a mammal in need thereof a therapeutically effect amount of an EP3 antagonist, where the EP3 antagonist is a compound of Formula I or pharmaceutically acceptable salt thereof. The invention further provides a method of improving insulin secretion where the mammal in need thereof is a diabetic patient.

In another embodiment, the invention provides a method for treating diabetes with an antagonist of the EP3 receptor. In yet another embodiment, the invention provides a method for treating Type II diabetes with an antagonist of the EP3 receptor. Another embodiment of the invention provides a method of treating diabetes, and specifically Type II diabetes with an antagonist of the EP3 receptor, where the antagonist is a compound of Formula I, or a pharmaceutically acceptable salt thereof.

In another embodiment, the invention provides a method for treating conditions or diseases in which an antagonist of the EP3 is involved by administering a therapeutically effective amount of a compound of Formula I or a pharmaceutically acceptable salt thereof, and a pharmaceutically acceptable carrier, to a mammal in need thereof. In another embodiment, the invention provides a method for treating conditions or diseases in which an antagonist of the EP3 is involved by administering a therapeutically effective amount of any embodiment of a compound of Formula I or a pharmaceutically acceptable salt thereof, and a pharmaceutically acceptable carrier, to a mammal in need thereof. Non-limited examples of such conditions or diseases include any one or combination of the following: bladder overactivity, cerebrovascular disease, coronary artery disease, peripheral vascular disease, hypertension, congestive heart failure, myocardial infarction, stroke, hemorrhagic stroke, ischemic stroke, pulmonary hypertension, neurodegenerative disorders, pain, premature labor, restinosis, thrombosis, Type I diabetes, and/or Type II diabetes.

In another embodiment, the invention provides combination therapies wherein the compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided.

Combination Agents

The compounds of the present invention may be used, alone or in combination with other therapeutic agents, in the treatment of various conditions or disease states. The compound(s) of the present invention and other therapeutic agent(s) may be administered simultaneously (either in the same dosage form or in separate dosage forms) or sequentially.

The administration of two or more compounds "in combination" means that the two compounds are administered closely enough in time that the presence of one alters the biological effects of the other. The two or more compounds may be administered simultaneously, concurrently or sequentially. Additionally, simultaneous administration may be carried out by mixing the compounds prior to administration or by administering the compounds at the same point in time but as separate dosage forms at the same or different site of administration.

In another embodiment, the compounds of this invention are co-administered with any one or more additional therapeutic agent(s) as described herein. The combination agents are administered to a mammal in a therapeutically effective amount to treat the diseases and/or condition described herein, e.g., obesity, diabetes, and cardiovascular conditions such as anti-hypertensive agents and coronary heart disease.

The phrases "concurrent administration," "co-administration," "simultaneous administration," and "administered simultaneously" mean that the compounds are administered in combination.

Kits

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

In another embodiment, the invention relates to the novel intermediates useful for preparing the compounds of the invention.

Administration and Dosing

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The compounds of the invention may be administered orally. Oral administration may involve swallowing, so that the compound enters the gastrointestinal tract, or buccal or sublingual administration may be employed by which the compound enters the bloodstream directly from the mouth.

In another embodiment, the compounds of the invention may also be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

Suitable subjects according to the present invention include mammalian subjects. Mammals according to the present invention include canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

Pharmaceutical Compositions

For the treatment of the diseases or conditions referred to herein, the compounds of the invention may be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (i.e., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, B. C. Finnin and T. M. Morgan, J. Pharm. Sci., vol. 88, pp. 955-958, 1999.

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients (3rd Ed.), American Pharmaceutical Association, Washington, 1999.

Compounds of the present invention may be synthesized by the methods described below, together with synthetic routes that include processes analogous to those well-known in the chemical arts, or modifications and transformations that are familiar to those of ordinary skill in the art, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der Organischen Chemie*, 4, Aufl. ed. Springer-Verlag, Berlin, including supplements (also available via the *Beilstein* online database). Many of the compounds used herein, are related to, or are derived from compounds in which there is a large scientific interest and commercial need, and accordingly many such compounds are commercially available or are reported in the literature or are easily prepared from other commonly available substances by methods which are reported in the literature.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Examples discussed herein. Isolation and purification of the products is accomplished by standard procedures, which are known to a chemist of ordinary skill. It will be apparent to one skilled in the art that all of the synthetic transformations can be conducted in a precisely similar manner whether the materials are enantioenriched or racemic. Moreover the resolution to the desired optically active material may take place at any desired point in the sequence using well known methods such as described herein and in the chemistry literature.

The following represent abbreviations for chemicals, solvents and reagents used in this document:

"DMSO" refers to dimethylsulfoxide, "DCE" refers to 1,2-dichloroethane, "DMF" refers to N,N-dimethylformamide, "EtOAc" refers to ethyl acetate, "EtOH" refers to ethanol, "MeOH" refers to MeOH, "MeCN" refers to acetonitrile, "$CH_2Cl_2$" refers to methylene chloride, "DCM" refers to methylene chloride (dichloromethane), "NMP" refers to N-methyl-2-pyrrolidone, "PE" refers to petroleum ether, "MTBE" refers to methyl tert-butyl ether, "THF" refers to tetrahydrofuran, "KOAc" refers to potassium acetate, "KHMDS" refers to potassium bis(trimethylsilyl)amide, "LiHMDS" refers to lithium bis(trimethylsilyl)amide, "MeI" refers to methyl iodide, "NaOtBu" refers to sodium tert-butoxide, "$PtO_2$" refers to platinum oxide, "Pd (dppf)$Cl_2$" or "$PdCl_2$(dppf).$CH_2Cl_2$" refers to [1,1'-bis(diphenylphosphino)ferrocine] dichloropalladium(II) (1:1), "tert-BuLi" refers to tert-butyllithium, "TsOH.$H_2$O" refers to p-toluenesulfonic acid monohydrate, "TMSCl" refers to trimethylsilyl chloride, "aq." refers to aqueous, "TFA" refers to trifluoroacetic acid, "MeONa" refers to sodium methoxide, "$Et_3N$" refers to triethylamine, "s-BuLi" refers to sec-butyllithium, "2-MeTHF" refers to 2-methyltetrahydrofuran, "KOt-Bu" refers to potassium tert-butoxide, "2-PrOH" refers to 2-propanol, 1-PrOH refers to 1-propanol, "HOAc" refers to acetic acid, "1-BuOH" refers to 1-butanol, "BuOAc" refers to butyl acetate, "COD" refers to 1,4-cyclooctadiene, "OMe" refers to methoxy, "nBuLi" refers to n-butyllithium, "Si gel" refers to silica gel, "OAc" refers to acetoxy, "Ph" refers to phenyl, "dba" refers to dibenzylidene acetone, "Xantphos" refers to 4,5-bis(diphenylphosphino)-9,9-dimethylxanthene, "XPhos-Pd-G2" refers to chloro(2-dicyclohexylphosphino-2',4',6'-triisopropyl-1,1'-biphenyl)[2-(2'-amino-1,1'-biphenyl)]palladium(II), "dppf" refers to 1,1'-bis(diphenylphosphino)ferrocene, "ca." refers to circa, "mp" refers to melting point, "$[\alpha]_D$" refers to specific rotation measured at the sodium D line, "c" refers to concentration in the units centigrams of solute per milliliter of solution, "$MgSO_4$" refers to magnesium sulfate, "Pd $(PPh_3)_4$" refers to tetrakis(triphenylphosphino)palladium(0).

The following abbreviations include units. The terms "room temperature," "ambient temperature," and/or "rt" refer to a temperature between 18 to 25° C. and "° C." refers to degrees Celsius, "K" refers to Kelvins, "nm" refers to nanometer, "mm" refers to millimeter, "Å" refers to angstroms, "µm" refers to micrometer, "pM" refers to picomolar, "µM" refers to micromolar, "mM" refers to millimolar, "M" refers to molar, "mmol" refers to millimoles, "mol" refers to moles, "µg" refers to micrograms, "mg" refers to milligrams, "g" refers to grams, "kg" refers to kilograms, "µL" refers to microliters, "mL" refers to milliliters, "L" refers to liters, "Psi" refers to pounds per square inch, "psig" refers to pounds per square inch above atmosphere pressure, "mbar" refers to milibars, "h" refers to hour, "min." refers to minute, "w/v" refers to concentration (mass of solute/volume of solution), "w/w" refers to concentration (mass of solute/mass of solution), "v/v" revers to concentration (volume of solute/volume of solvent), "Anal." refers to microanalysis, "Calcd" refers to calculated, "rpm" refers to revolutions per minute, "pH" refers to potential hydrogen.

The following abbreviations address spectroscopy and chromatography. "NMR" refers to nuclear magnetic resonance spectroscopy, "CDCl$_3$" refers to deuterated chloroform, "CD$_3$OD" refers to deuterated methanol, "MHz" refers to megahertz, "s" refers to singlet, "d" refers to doublet, "t" refers to triplet, "q" refers to quartet, "dd" refers to doublet of doublets, "ddd" refers to doublet of doublet of doublets, "td" refers to triplet of doublets, "dt" refers to doublet of triplets, "br. s." refers to broad singlet, "m" refers to multiplet, "H" refers to proton, "MS" refers to mass spectrometry, "ESI" refers to electrospray ionization, "APCI" refers to atmospheric pressure chemical ionization, "SFC" refers to super critical chromatography, "CO$_2$" refers to carbon dioxide, "HPLC" refers to high performance liquid chromatography, "MPLC" refers to medium pressure liquid chromatography, "TLC" refers to thin layer chromatography, "ORTEP" refers to Oak Ridge Thermal-Ellipsoid Plot, "EI" refers to electron impact ionization, "GCMS" refers to gas chromatography-mass spectrometry, "m/z" refers to a mass to charge ratio, "LCMS" refers to liquid chromatography-mass spectrometry, "HPLC" refers to high performance liquid chromatography, "R$_f$" refers to a retention factor, "MPLC" refers to medium pressure liquid chromatography, "CV" refers to column volumes, "t$_R$" refers to retention time, "TLC" refers to thin layer chromatography.

Experiments were generally carried out in air or under an inert atmosphere (nitrogen or argon), particularly in cases where oxygen- or moisture-sensitive reagents or intermediates were employed. Concentration in vacuo means that a rotary evaporator was used. Unless otherwise noted, chemical reactions were performed at room temperature.

Commercial solvents and reagents were generally used without further purification, including anhydrous solvents where appropriate (generally DriSolv products from EMD Millipore, Billerica, Mass., or Sure-Seal™ products from the Aldrich Chemical Company, Milwaukee, Wis.). Reaction progress was monitored using TLC, LCMS, HPLC, and/or GCMS analyses. Products were generally dried under vacuum before being carried on to further reactions or submitted for biological testing. Proton nuclear magnetic spectroscopy ($^1$H NMR) was recorded with 400,500, or 600 MHz spectrometers. Chemical shifts are expressed in parts per million (ppm, δ) referenced to residual peaks from the deuterated solvents employed. Mass spectrometry (MS) data is reported from either liquid chromatography-mass spectrometry (LCMS) via electrospray ionization or atmospheric pressure chemical ionization sources or from gas chromatography-mass spectrometry (GCMS) instrumentation via electron impact ionization sources. Silica gel chromatography was performed primarily using a medium pressure system using columns pre-packaged by various commercial vendors. Microanalyses were performed by Quantitative Technologies Inc.

Chromatographic retention times were measured on LCMS and HPLC systems. Method A refers to an LCMS system employing a Waters Atlantis dC18 4.6×50 mm column (5 µm particle size), eluted using a gradient of MeCN in H$_2$O, modified with 0.05% (v/v) TFA. Elution, at a rate of 2.0 mL/min., was commenced at 5.0% MeCN and linearly ramped to 95% MeCN over 4.0 min., after which it was held at 95% MeCN for 1.0 min. Method B refers to an HPLC system employing an XBridge C18 4.6×150 mm column (5 µm particle size), eluted using a gradient of MeCN in H$_2$O, modified with 0.1% (v/v) TFA. Elution, at a rate of 1.5 mL/min., was commenced at 5% MeCN. After 1.5 min, the MeCN component of the eluent was linearly ramped to 100% over 8.5 min. and further held at 100% MeCN for 1 min. Method C refers to an LCMS system employing a Waters Sunfire C18 4.6×50 mm column (5 µm particle size); eluted using a gradient of MeCN in H$_2$O, modified with 0.05% (v/v) TFA. Elution, at a rate of 2.0 mL/min., was commenced at 10% MeCN and linearly ramped to 30% MeCN over 4.0 min., after which it was held at 95% MeCN for 1.0 min.

The terms "concentrated" and "evaporated" refer to the removal of solvent at reduced pressure on a rotary evaporator with a bath temperature less than 60° C. Unless indicated otherwise, percent is percent by weight given the component and the total weight of the composition, specific temperatures are in ° C., and pressure is at or near atmospheric pressure.

The compounds and intermediates described below were named using the naming convention provided with ChemBioDraw Ultra, Version 13.0 (CambridgeSoft Corp., Cambridge, Mass.). The naming convention provided with ChemBioDraw Ultra, Version 13.0 are well known by those skilled in the art and it is believed that the naming convention provided with ChemBioDraw Ultra, Version 13.0 generally comports with the IUPAC (International Union for Pure and Applied Chemistry) recommendations on Nomenclature of Organic Chemistry and the CAS Index rules.

For syntheses referencing procedures in other Examples or Methods, reaction conditions (length of reaction and temperature) may vary. Purifications may vary between experiments: in general, solvents and the solvent ratios used for eluents/gradients were chosen to provide appropriate TLC R$_f$'s or chromatographic t$_R$'s.

EXAMPLES

In the preparation of the Formula I compounds it is noted that some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-t-butoxycarbonyl (Boc), benzyloxycarbonyl (Cbz), and 9-fluorenylmethylenoxycarbonyl (Fmoc) for amines and lower alkyl or benzyl esters for carboxylic acids) which are generally not chemically reactive under the reaction conditions described and can typically be removed without chemically altering other functionality in the Formula I and Ia compounds.

The Reaction Schemes described below are intended to provide a general description of the methodology employed in the preparation of the compounds of the present invention. Some of the compounds of the present invention contain a single chiral center with stereochemical designation (R). It will be apparent to one skilled in the art that all of the synthetic transformations can be conducted in a precisely similar manner whether the materials are enantioenriched or racemic. Moreover the resolution to the desired optically active material may take place at any desired point in the sequence using well known methods such as described herein and in the chemistry literature.

In the Reaction Schemes that follow, the variables X, Y, $R^1$, $R^2$, $R^3$, m and n are as described in the summary except where otherwise noted.

Reaction Scheme I outlines general procedures that can be used to provide compounds of the present invention having Formula (Ia) and (Ib).

methods described in the literature such as: *Heterocyclic Chemistry in Drug Discovery* 2013, 471-534; *Mod. Het. Chem.* 2011, 3, 1527-1629; *J. Organomet. Chem.* 2014, 768, 75-114., *Adv. Synth. Catal.,* 2006, 348, 686-690, or methods described below (Reaction Scheme II-IV). Intermediates (2) are commercially available or may be synthesized from intermediate (1) via methods known to those skilled in the art, in the literature such as *Tetrahedron* 2011, 67, 576-583, or through methods described below (Reaction Scheme II-IV). Intermediates (3) and (4) may be prepared via methods those skilled in the art or methods described below (Reaction Scheme V-VI).

Reaction Scheme I

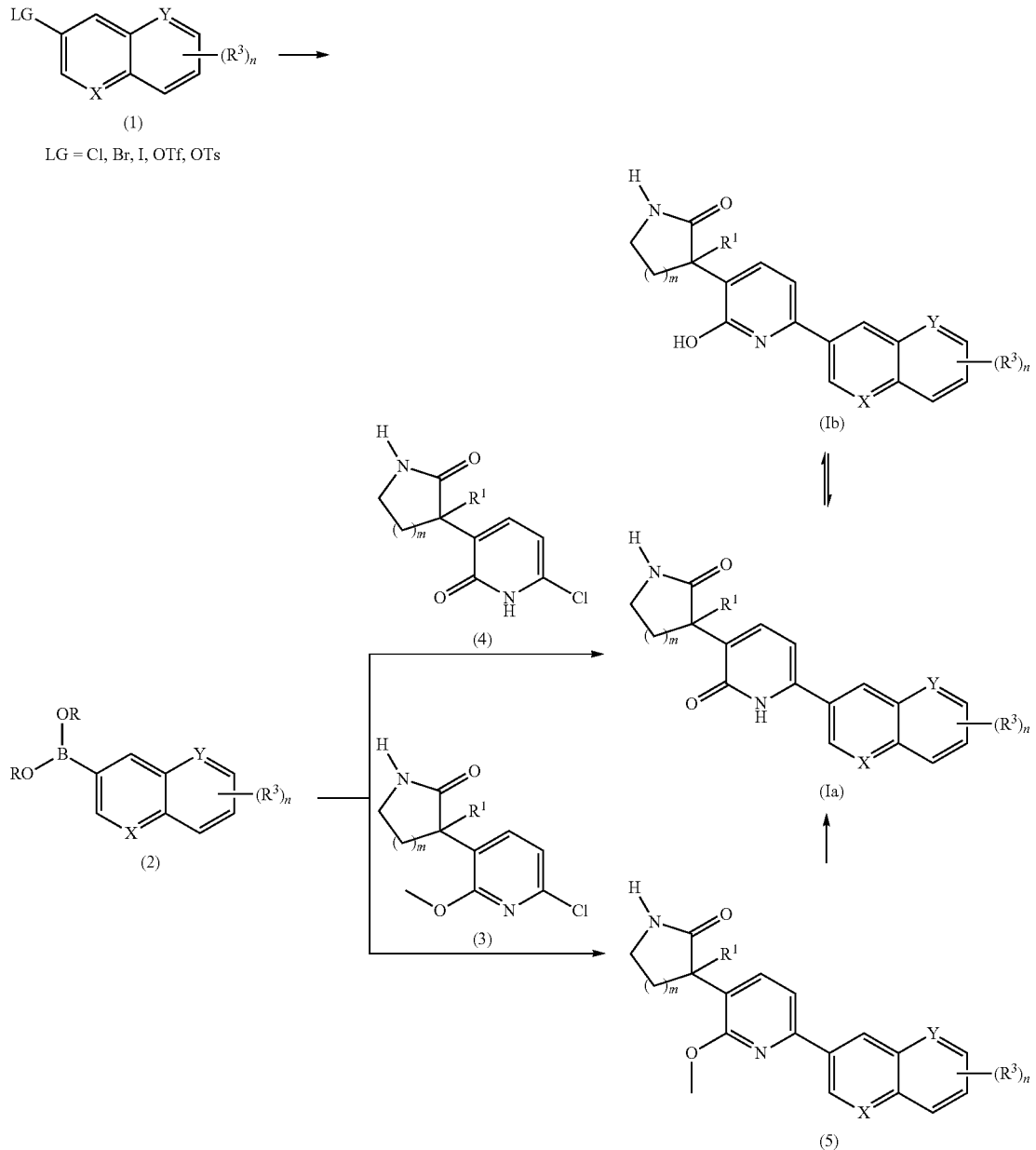

Intermediates (1) are commercially available or may be synthesized from the appropriate starting materials using Compounds of Formula (Ia) and (Ib) may be synthesized from intermediate (4) and a boronic acid derivative (2) via metal-catalyzed cross-coupling reactions described in the literature such as: *Metal Catalyzed Cross-Coupling Reactions and More*, Wiley-VCH, Weinheim, Germany, 2014, 3, 995; *Applications of Transition Metal Catalysis in Drug Discovery and Development*, John Wiley & Sons, Inc., Hoboken, N.J., USA, 2012, 3, 97. For example, compounds of Formula (Ia) and (Ib) may be prepared through a Suzuki-Miyaura cross-coupling reaction using a palladium catalyst such as $PdCl_2(dppf).CH_2Cl_2$, palladium(II) acetate, or $Pd(PPh_3)_4$, in the presence of a suitable ligand such as di(1-adamantyl)-n-butylphosphine (CataCXium®A), and a base such as sodium carbonate, sodium bicarbonate, or cesium fluoride, in a reaction inert solvent such as 2-PrOH, 1-BuOH, DMF, 1,4-dioxane, water, or mixture thereof, at a temperature between 20° C. and 130° C.

Alternatively, compounds of Formula (Ia) and (Ib) may be synthesized from the intermediate (5) via methods known to those skilled in the art. For example, compounds of Formula (Ia) and (Ib) may be synthesized from the intermediate (5) using iodo trimethylsilane in MeCN at a temperature between 0° C. and 35° C., or using sodium n-propane thiolate or ethyl sodium thiolate in DMF at a temperature between 20° C. and 120° C.

Intermediate (5) may be prepared from the intermediate (3) through metal catalyzed cross-coupling reactions known to those skilled in the art. For example, intermediate (5) may be prepared from intermediate (3) and a boronic acid derivative (2) in a Suzuki-Miyaura cross-coupling reaction using a palladium catalyst such as $PdCl_2(dppf).CH_2Cl_2$, in a reaction inert solvent such as 1,4-dioxane, water or mixture thereof, in the presence of a base such as sodium carbonate at a temperature between 20° C. and 120° C.

Reaction Scheme II

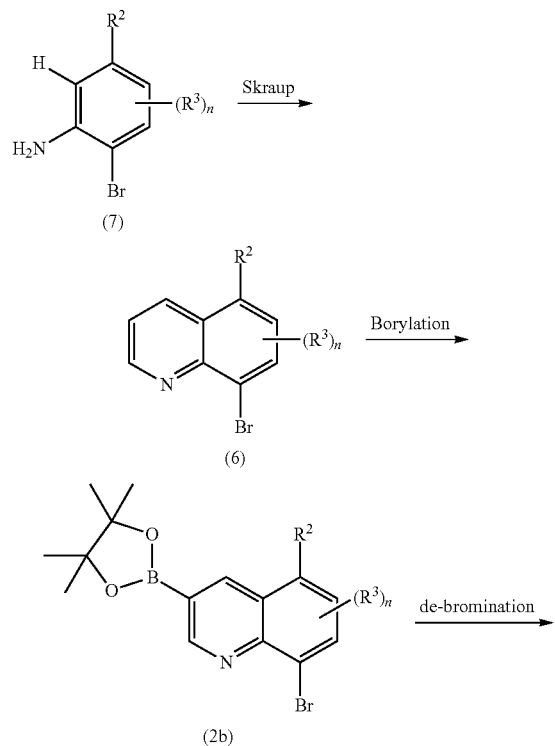

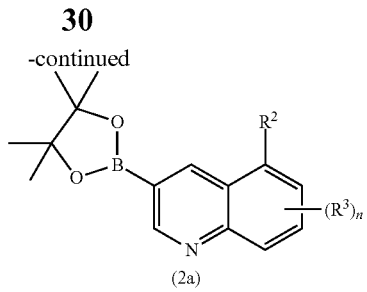

Reaction Scheme II outlines the synthesis of intermediates (2a), a subset of intermediates (2). Compounds of Formula (2a) may be synthesized from intermediate (6) via a borylation of bromoquinoline intermediate (6) followed by de-bromination of intermediate (2b). Intermediates (2a) may be prepared from intermediate (2b) via de-bromination reaction using the methods known to those skilled in the art. For example, intermediates (2a) may be synthesized from intermediate (2b) through a de-bromination reaction using a catalyst such as palladium on carbon, or palladium(II) hydroxide, using reducing agents such as hydrogen gas, ammonium formate, formic acid, or 1,4-cyclohexadiene, and a base such as pyridine, $Et_3N$, or potassium carbonate, in a reaction inert solvent such as EtOH, EtOAc, THF, or MeOH at a temperature between 10 and 80° C.

Intermediate (2b) may be prepared from a metal-catalyzed C—H borylation reaction of bromoquinoline intermediate (6) as described in literature such as: *Tetrahedron Lett.* 2002, 43, 5649-5651, or *Top Organomet Chem* 2011, 34, 139-168. For example, intermediate (2b) may be synthesized via an iridium-catalyzed C—H borylation reaction using an iridium catalyst such as bis(1,5-cyclooctadiene(di-µ-methoxodiiridium(I) ($[Ir(COD)(OMe)]_2$), or bis(1,5-cyclooctadiene)diiridium(I) dichloride ($[IrCl(COD)]_2$), in the presence of a suitable ligand such as 4,4'-di-tert-butyl bipyridine or 2,2'-bipyridine, and a borane agent such as bis (pinacolato)diboron or pinacolborane, in a reaction inert solvent such as heptanes at a temperature between room temperature and 100° C.

Bromoquinoline intermediate (6) can be prepared via a Skraup reaction starting from bromoaniline intermediate (7) using methods known in literature such as: *Mod. Het. Chem.* 2011, 3, 1527-1629. For example, bromoquinoline intermediate (6) can be prepared from bromoaniline intermediate (7) by a reaction with glycerin in nitrobenzene and strong acids (i.e. sulfuric acid) at 140° C. Alternatively, bromoquinoline intermediate (6) can be synthesized from bromoaniline intermediate (7) via metal-catalyzed reactions as described in the literature such as: *J. Organomet. Chem.* 2014, 768, 75-114. Bromoaniline (7) are commercially available or may be prepared by methods known to those skilled in the art.

Reaction Scheme III

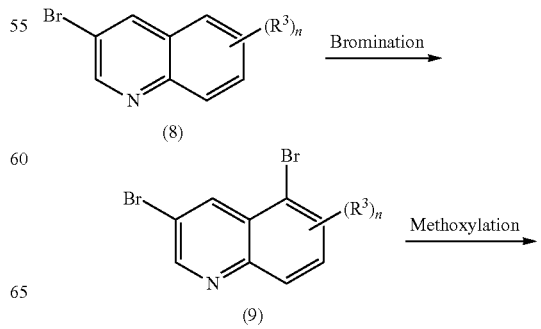

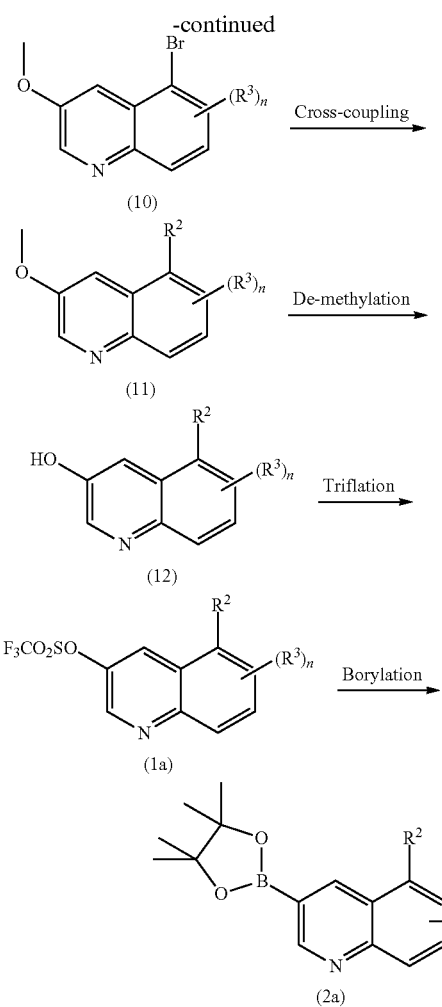

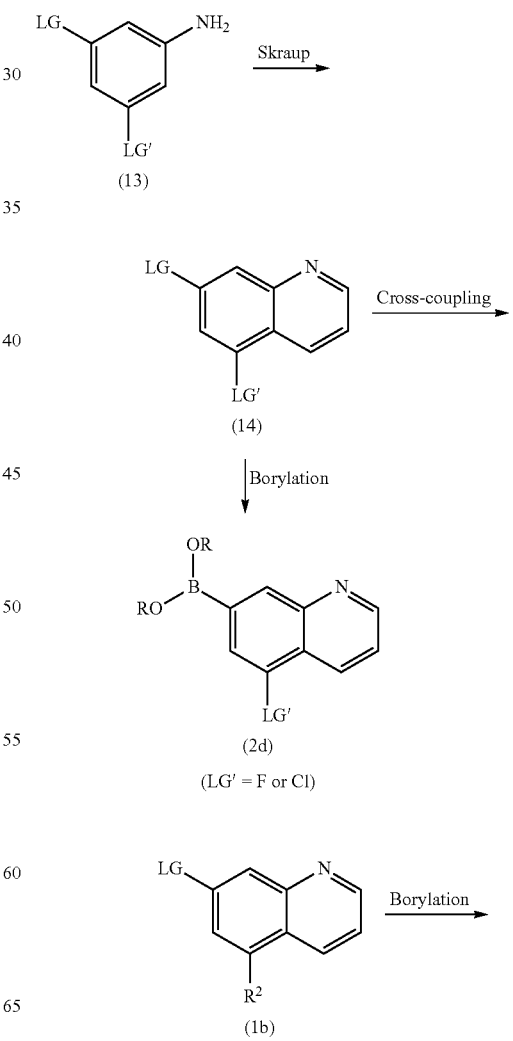

(LG' = F or Cl)

Reaction Scheme III outlines an alternative synthesis of intermediates (2a), a subset of intermediates (2). Intermediate (2a) can be prepared via a metal-catalyzed borylation reaction starting from intermediate (1a). For example, intermediate (2a) may be synthesized using a palladium catalyst such as $Pd_2(dba)_3$ or $PdCl_2(dppf).CH_2Cl_2$, in the presence of a suitable ligand such as 2-dicyclohexylphosphino-2',4',6'-triisopropylbiphenyl, and a base such as KOAc, and a borane reagent such as pinacolborane or bis(pinacolato) diboron in a reaction inert solvent such as 1,4-dioxane at a temperature between room temperature and 100° C. Intermediate (1a) can be synthesized using methods known to those skilled in the art. For example, intermediate (1a) may be prepared using trifluoromethanesulfonyl chloride, trifluoromethanesulfonic anhydride, or N-phenyltriflimide, and a base such as pyridine, $Et_3N$, or N,N-diisopropylethylamine in a solvent such as DCM at a temperature between 0° C. to room temperature. The methoxy group in intermediate (11) can be deprotected to provide intermediate (12) via a de-methylation reaction under conditions well known to those skilled in the art. For example, intermediate (12) may be synthesized using lithium chloride and p-toluenesulfonic acid in a solvent such as NMP. Intermediate (11) may be synthesized via a metal-catalyzed cross-coupling reaction starting from intermediate (10) using methods described in literature such as: *Metal Catalyzed Cross-Coupling Reactions and More*, Wiley-VCH, Weinheim, Germany, 2014; *J.* *Org. Chem.* 1997, 62, 8681-8686. For example, intermediate (11) where $R^2$ is methyl may be prepared via a palladium-catalyzed Suzuki-Miyaura cross-coupling reaction using a palladium catalyst such as $Pd(dppf)Cl_2$, in the presence of a base such as cesium carbonate, and an appropriate boronic acid derivative such as 2,4,6-trimethyl-1,3,5,2,4,6-trioxatriborinane, in a reaction inert solvent such as 1,4-dioxane. Intermediate (10) may be synthesized via a methoxylation of dibromoquinoline intermediate (9) using methods known to those skilled in the art. For example, intermediate (10) can be synthesized from dibromoquinoline intermediate (9) with MeONa in 1,3-dimethyl-3,4,5,6-tetrahydro-2(1H)-pyrimidinone at 120° C., heating in the presence of MeONa and copper powder at 135° C., or using palladium-catalyzed methoxylation reaction as described in *Chem. Eur. J.* 2012, 18, 2498-2502. Dibromoquinoline intermediate (9) can be prepared from bromoquinoline intermediate (8) via a bromination using methods known to those skilled in the art. For example, dibromoquinoline intermediate (9) may be prepared from bromoquinoline intermediate (8) using N-bromosuccinimide in the presence of $H_2SO_4$ in a reaction solvent such as DCM at room temperature. Bromoquinoline intermediate (8) are commercially available, or can be synthesized using methods known to those skilled in the art.

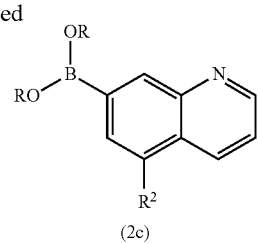

LG = I, Br, Cl, OTf
LG' = I, Br, Cl, F, OTf

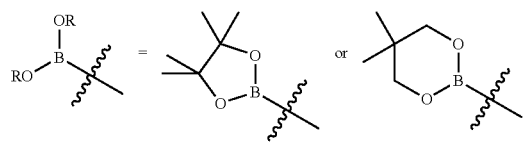

Reaction Scheme IV outlines a synthesis of intermediates (2c) and (2d), a subset of intermediates (2). Intermediate (2c) ($R^2$=alkyl, cycloalkyl) can be synthesized via a borylation reaction with intermediate (1b) using methods known to those skilled in the art or methods described in Reaction Schemes II-III above. For example, intermediate (2c) can be synthesized via a palladium-catalyzed borylation reaction using a palladium catalyst such as XPhos-Pd-G2, in the presence of a borane agent such as pinacol borane, and a base such as KOAc in a reaction solvent such as 1,4-dioxane at a temperature between room temperature and 100° C. Intermediate (1 b) can be synthesized via a metal-catalyzed cross-coupling reaction starting from intermediate (14) using methods known to those skilled in the art. For example, intermediate (1b) may be prepared via a Suzuki-Miyaura cross-coupling reaction using a palladium catalyst such as XPhos-Pd-G2 or $PdCl_2$(dppf).$CH_2Cl_2$, in the presence of a base such as sodium carbonate or cesium carbonate, and a suitable boronic acid derivative or a potassium trifluoroborate, in a reaction inert solvent such as 1,4-dioxane, toluene, water, or a mixture thereof, at a temperature between room temperature and 110° C. Intermediate (14) can be synthesized via a Skraup reaction from aniline (13) using methods described in Reaction Scheme II. When groups LG and LG' are different, it may form a regioisomer of intermediate (14), which may be separated by methods known to those skilled in the art at appropriate step of the reaction sequence. Anilines (13) are commercially available or can be synthesized by methods known to those skilled in the art.

Intermediate (2d, LG'=F or Cl) can be synthesized from intermediate (14, LG'=F or Cl) via a metal-catalyzed borylation reaction using methods described above. Intermediate (14, LG'=F or Cl) may be synthesized from aniline (13, LG'=F or Cl) via a Skraup reaction described above.

Reaction Scheme V

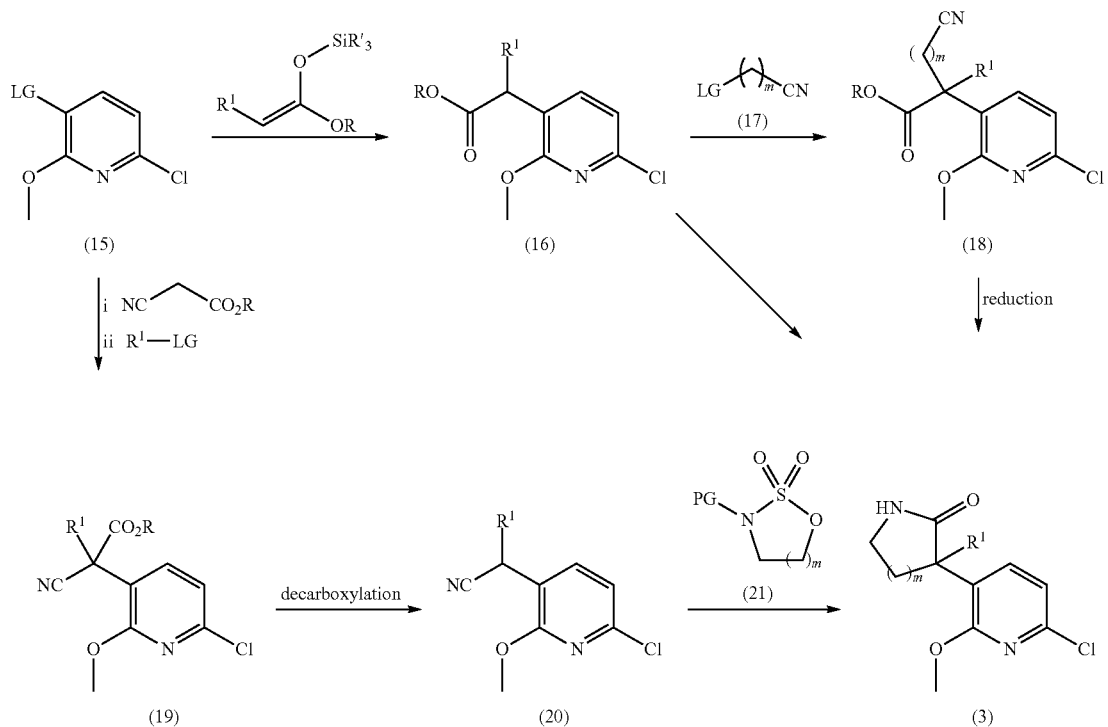

PG = protecting group
LG = Cl, Br, I, OTf, OTs
R, R' = alkyl

Reaction scheme V outlines a synthesis of intermediate (3). Intermediate (3) may be synthesized from intermediate (18) by a reduction of the nitrile by any number of reduction conditions known to those skilled in the art. For example, intermediate (3) may be prepared from intermediate (18) using a metal catalyst such as Raney-Nickel catalyst, under an atmosphere containing hydrogen, in a reaction inert solvent such as EtOH or MeOH at a temperature ranging from 25° C. to 90° C. Intermediate (18) may be prepared by alkylation of intermediate (16) with an appropriate alkylating agent (17), using an appropriate base, for example, alkali-metal amide bases or alkali-metal alkoxide bases under inert reaction solvents such as THF, 1,4-dioxane, or toluene at a temperature of −78° C. to room temperature. For example, intermediate (18) may be prepared by treatment of intermediate (16) with lithium hexamethydisilylamide in THF followed by the addition of an appropriate alkyl halide at −78° C. and subsequent warming to 25° C. Intermediate (16) can be prepared by an arylation reaction of an appropriate silyl ketene acetal derivative with intermediate (15) using transition metal catalysis such as palladium or nickel such as methods described in *J. Am. Chem. Soc.* 2003, 11176. For example, intermediate (16) may be prepared from intermediate (15) using tris(dibenzylideneacetone)dipalladium(0) as a catalyst, in the presence of a ligand such as tri-tert-butylphosphine or Xantphos and an appropriate silyl ketene acetal derivative such as (E)-(1-methoxyprop-1-enyloxy)trimethylsilane, and an additive such as zinc (II) fluoride, in reaction inert solvents such as THF, 1,4-dioxane, or DMF at a temperature ranging from 25° C. to 110° C. Intermediate (15) are either commercially available or may be synthesized by methods known to those skilled in the art.

Alternatively, intermediate (3) may also be prepared by alkylation of intermediate (16) with an alkylating agent (21) (*Angew. Chem. Int. Ed.* 2010, 568; *Chem. Eur. J.* 2013, 3071; *Bioorg. Med. Chem. Lett.* 2010, 5713; *Synlett* 2012, 2408), where PG is a protecting group such as a tert-butoxycarbonyl group, using an appropriate base such as sodium hexamethyl disilylamide or KOt-Bu in a reaction inert solvent such as THF, 1,4-dioxane or toluene at a temperature ranging from −78° C. to 25° C. A subsequent liberation of a protecting group (PG) under either acidic or basic conditions, known to those skilled in the art, would then provide intermediate (3).

Alternatively, intermediate (3) may be prepared by alkylation of intermediate (20) with an alkylating agent (21) in a manner analogous to alkylation of intermediate (16), followed by a hydrolysis using a base, such as sodium hydroxide, in reaction inert solvents such as MeOH and THF. Intermediate (20) may be prepared by a decarboxylation reaction of intermediate (19) using any number of reaction conditions known to those skilled in the art. For example, intermediate (20) may be prepared by heating the intermediate (19) in a reaction inert solvent such as DMSO or DMF that contain water at a temperature between 50° C. and 150° C. Intermediate (19) may be prepared by a metal-catalyzed arylation reaction of an appropriate alkyl cyano acetate derivative with intermediate (15), followed by an alkylation reaction of the resulting arylated product by methods known to those skilled in the art. For example, intermediate (19) can be synthesized from intermediate (15) and tert-butyl cyanoacetate using a palladium catalyst such as Pd(dppf)Cl$_2$, in the presence of a base such as NaOtBu, in a reaction inert solvent such as 1,4-dioxane or THF at 80° C., followed by an alkylation reaction of the resulting product with iodomethane.

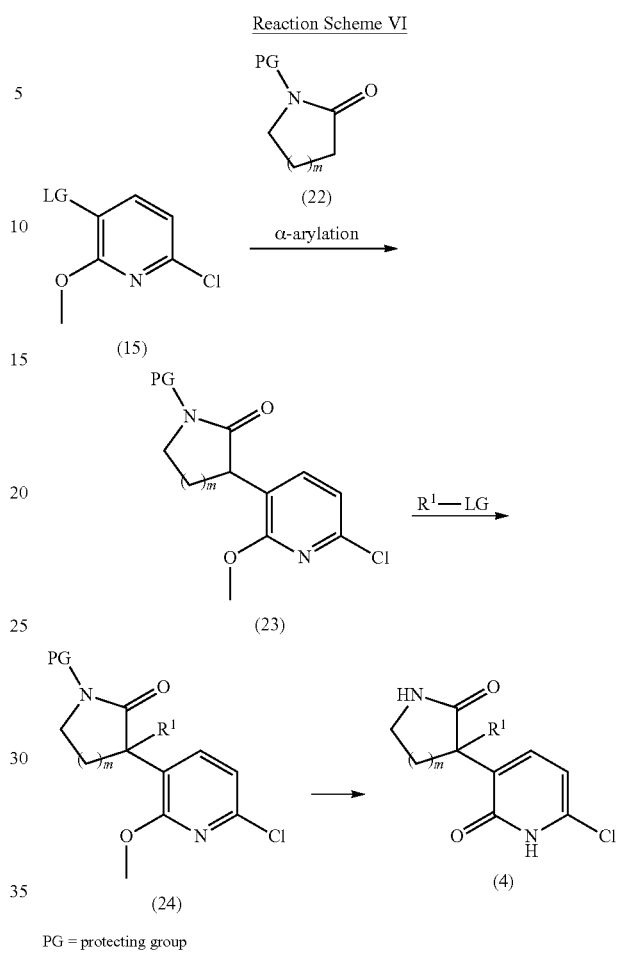

PG = protecting group
LG = Cl, Br, I, OTf, OTs

Reaction scheme VI outlines a synthesis of intermediate (4). Intermediate (4) may be prepared by removal of the protecting group (PG) and the methyl group from intermediate (24) by any number of methods known to those skilled in the art. For example intermediate (4) may be prepared from intermediate (24) using trifluormethanesulfonic acid in a reaction inert solvent such as DCE at a temperature between 40° C. and 140° C.

Intermediate (24) may be prepared by an alkylation reaction of intermediate (23) using a suitable alkylation agent R$^1$-LG, using any number of suitable bases such as metal amide bases, such as lithium hexamethyldisilylamide or alkoxide bases such as KOt-Bu in a reaction inert solvent such as THF, 1,4-dioxane, or toluene. Intermediate (23) may be synthesized by an arylation reaction of intermediate (22) with intermediate (15) using a palladium or nickel catalyst with an appropriate ligand such as methods described in *Org. Lett.* 2003, 3037. For example, intermediate (23) can be synthesized from intermediate (22) and intermediate (15) using tris(dibenzylideneacetone)dipalladium(0) as a catalyst with a ligand such as tri-tert-butylphosphine or Xantphos with zinc (II) fluoride in reaction inert solvents such as THF, 1,4-dioxane, or DMF at a temperature ranging from 25° C. to 110° C. Intermediate (22) are commercially available or may be prepared by methods known to those skilled in the art.

Intermediates

Intermediate 1 (R)-6-Chloro-3-(3-methyl-2-oxopiperidin-3-yl)pyridin-2(1H)-one

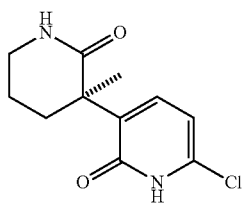 [SMILES: C[C@]1(c2ccc(Cl)[nH]c2=O)CCCNC1=O]

Step 1. 2,6-Dichloropyridin-3-amine: 3-Nitro-2,6-dichloropyridine (1.34 kg, 6.95 mol) and ammonium chloride (3.00 kg, 56.1 mol) were suspended/dissolved in a solution of MeOH (12 L) and water (2.4 L). Iron powder (2.54 kg, 45.5 mol, 70 mesh) was added, and the resulting dark grey mixture was heated to reflux (70.8-72.4° C. internal temperature over the course of the reaction) under nitrogen with stirring. After 2.0 h, the mixture had become a dark, red-brown color. Heating was suspended, and more iron powder (532 g 9.53 mol, 70 mesh) was added. Refluxing was then resumed. After 2.0 h, heating was again suspended, iron powder (549 g, 9.83 mol, 70 mesh) was added, and refluxing was resumed. A final addition of iron powder (261 g, 4.67 mol, 70 mesh) was made 2.0 h later, and refluxing was continued subsequently for 14 h. After cooling to ca. 40° C., the reaction mixture was filtered over Celite®. The filter cake was rinsed with MeOH (7×2 L), and the combined filtrates were concentrated under reduced pressure to give a dark green solid. (Care must be taken so that the filter cakes do not run dry; unreacted iron powder is reactive towards oxygen and can ignite a fire.) The solid was partitioned between EtOAc (14 L) and water (9 L), and the aqueous phase was further extracted with EtOAc (2×5 L). The combined organic phases were washed with water (2×3 L) and brine (3 L) and dried over $Na_2SO_4$. The aqueous phases were filtered through Celite®, and the residual organic phases were isolated. All of the organic phases were combined, filtered through Celite®, and evaporated under reduced pressure to afford 2,6-dichloropyridin-3-amine as a beige solid (1050 g, 92.6%), which was used in the next step without further purification.

Step 2. 6-Chloro-2-methoxypyridin-3-amine: A 50 L reactor, maintained under a nitrogen atmosphere, was charged with 2,6-dichloropyridin-3-amine (3.13 kg, 19.2 mol), THF (9 L) and MeONa/MeOH solution (18.3 L, 97.6 mol, 30% w/w). The mixture was heated to reflux (71.9-72.9° C. internal temperature over the course of the reaction) and maintained at this temperature overnight. Subsequently a portion (ca. 15 L) of the reaction solvent was removed by distillation under reduced pressure (pressure gradually reduced to 250 mbar, heating temperature maintained at 80° C., internal temperature dropped from 71° C. to 61° C.). The reaction mixture was then cooled to an internal temperature of 35° C., and ice/water (16 L) was added in 4 portions (an exotherm was observed after addition of the first portion). The resulting mixture was then extracted with DCM (20 L and then 4×6 L). The combined organic phases (ca. 50 L) were washed with water (portions up to 20 L were separately washed with 3 L of water each). The combined water washings were back extracted with DCM (2×1.5 L). The combined organic phase (ca. 55 L) was washed with brine (3 L), dried over $Na_2SO_4$, and concentrated under reduced pressure to give 6-chloro-2-methoxypyridin-3-amine as a brown solid (2.87 kg, 94.4%), which was used in the next step without purification.

Step 3. 3-Bromo-6-chloro-2-methoxypyridine: A 50 L reactor, equipped with 1 L dropping funnel, was charged with 6-chloro-2-methoxypyridin-3-amine (1.12 kg, 7.04 mol) and water (7.8 L). Cooling was set at −10° C., and 48% aqueous HBr (10.0 L) was added at once to the stirred brown suspension. The internal temperature rose to 24° C., and the solid dissolved to afford a dark red-brown solution. After the internal temperature dropped to −3.5° C., a solution of sodium nitrite (492 g, 7.13 mol) in water (3.7 L) was added dropwise at such a rate (total addition time of 1.5 h) that the internal temperature was maintained between −2.0 and −1.5° C. The cooling temperature was then set at −6° C., and the mixture was stirred for 1.5 h at −3.5 to −4.5° C. Meanwhile, copper(I) bromide (1.12 kg, 7.79 mol) was suspended in water (1.35 L), and 48% aqueous HBr (6.28 L) was added; the mixture was stirred until all copper(I) bromide had dissolved. The reactor's cooling was then returned to −10° C., and the copper(I) bromide/aqueous HBr solution prepared above was added dropwise to the reaction mixture, maintaining the internal temperature between −4.5 and −3.3° C. After 1.5-2 L of the solution was added, a thick (ca. 15 cm) layer of foam had appeared. Toluene (100 mL) was added, which caused the foam to break up. The addition of the copper(I) bromide/aqueous HBr solution was then completed (total addition time of 1.75 h). After complete addition, the internal temperature was raised to 5° C. over the course of 1 h; evolution of gas was observed via a bubbler. The internal temperature was further raised to 15° C. over an additional 1 h. Again, a foam started to appear, but faster stirring (220-250 rpm) broke it up. The internal temperature was raised to 30° C. over the next 1 h, and the reaction mixture was stirred at this temperature overnight. The reaction mixture was then cooled to 17° C., and water (10 L) was added. The mixture was extracted with DCM (14.5 L followed by 3×5 L, vigorous stirring each time for 5 min at 350 rpm). The combined organic phases were washed with brine (5 L), dried over $Na_2SO_4$, and concentrated under reduced pressure to give 3-bromo-6-chloro-2-methoxypyridine as a brown-purple solid (1.52 kg, 97%). Two similar batches were run yielding 1.52 kg and 1.36 kg of crude product.

The three crude product batches were combined (4.40 kg), dissolved in DCM (3.5 L), and purified by silica gel column chromatography (10 Kg, eluted with 100% DCM) to afford a light orange solid (4.33 kg, 98.4% recovery).

The solid was dissolved in MeOH (4 L) with stirring in a 65° C. bath. Active cooling was applied, and the product came out as a thick, massive layer. MeOH (500 mL) was added and heat was applied to completely redissolve the solid. The resulting red-orange solution was cooled slowly with stirring. Fast crystallization occurred. After 2 h, the crystal mass was put on an 8 L P2 pore size (40-100 μm) frit and pressed well while under suction. The filter cake was rinsed with MeOH (2×1 L), and suction was applied to dry the solid. After 1.5 h, the filter paper was exchanged for a new one. Drying was continued (in air) overnight, thus affording the product (2920 g, 67.4% recovery). The crystals in the filtrate were collected on a frit, pressed, and subjected to suction. This product was rinsed with MeOH (300 mL) and subjected to further suction. The product (462 g, 10.7% recovery) was then dried overnight in air on sheets of filter paper. The filtrate (ca. 6 L) was concentrated to 1 to 1.5 L at 55 to 60° C. and allowed to return to rt. Crystallization occurred, and, after 4 h, the crystal mass was scraped loose and collected on a frit. The filter cake was pressed and subjected to suction, rinsed with MeOH (3×50 mL), and subjected further to suction. The solid was then scraped loose and dried under suction overnight. Similarly, fourth and fifth crops were isolated. In total, 3.86 kg (89.2% recovery for the crystallization) of 3-bromo-6-chloro-2-methoxypyridine was obtained for an overall yield 84%.

Step 4. (S)-5-Chloro-N-(1-phenylethyl)pentanamide: 5-Chlorovaleryl chloride (50. g, 0.32 mol) was added to a 0° C. mixture of (S)-1-phenylethan-1-amine (39.7 g, 42 mL, 0.32 mol) and Et₃N (50 mL) in THF (1 L), dropwise at a rate that caused the internal temperature to rise to 13° C. After stirring at rt overnight, the volatile components of the reaction were evaporated. EtOAc was added to the residue, and the resulting solution was washed sequentially with 2.0 M aqueous HCl (2×), saturated aqueous NaHCO₃, and brine. The organic layer was dried over Na₂SO₄ and evaporated to afford (S)-5-chloro-N-(1-phenylethyl)pentanamide (75 g, 97%), which was used without further purification.

Step 5. (S)-1-(1-Phenylethyl)piperidin-2-one: Sodium hydride (25 g, 0.63 mol, 60% dispersion in mineral oil) was added in portions to a solution of (S)-5-chloro-N-(1-phenylethyl)pentanamide (75 g, 0.31 mol) in THF (2.5 L). The reaction mixture was then heated to 57° C. (internal temperature) and maintained at this temperature overnight. After cooling the reaction mixture in a −10° C. bath, the reaction was quenched by addition of a saturated aqueous solution of ammonium chloride. The resulting mixture was stirred for 1 h, after the workup mixture was concentrated by rotary evaporation to remove most of the THF. EtOAc was added, and the organic layer was isolated. The organic layer was washed sequentially with water and brine, dried over Na₂SO₄, and concentrated until most of the EtOAc was removed. Heptanes and seeding crystals were then added to the solution, and the resulting white solid was collected by filtration, washed with cold heptanes, and dried under vacuum at 50° C., thus affording (S)-1-(1-phenylethyl)piperidin-2-one (53.5 g, 83%).

Step 6. 3-(6-Chloro-2-methoxypyridin-3-yl)-1-((S)-1-phenylethyl)piperidin-2-one: PdCl₂(Xantphos) (600 g) was stirred in DCM (6 L) at room temperature for 2 h, after which the slurry was filtered over a pad of Celite®. The solids were washed with DCM until the eluent was colorless. The filtrate and washings were combined and concentrated to ca. 3 L, and heptanes (6 L) was added to the residue. The catalyst was collected by filtration, washed with a DCM/heptanes mixture (600 mL), and dried under reduced pressure, affording a yellow solid (439 g, 73.2% recovery).

In a 50 L reactor, a solution of ((S)-1-phenylethyl)piperidin-2-one (1.60 kg, 7.88 mol) in THF (7.5 L) and degassed under reduced pressure. The pale amber solution was cooled to −10° C. (internal temperature) using a −20° C. bath, and s-BuLi solution in 92:8 cyclohexane/hexane (5.20 L, 6.76 mol, 1.3 M) was added slowly over 1.5 h, keeping the internal temperature between −8° C. and −5° C. When the addition was complete, the cold bath was set at −5° C., and the mixture was stirred for 0.75 h at −5° C. to 0° C. A solution of zinc(II) chloride in 2-MeTHF (4.00 L, 8.00 mol, 2.0 M) was added over 10 min., causing the internal temperature to rise from −2.5° C. to 10° C. Cooling was ended, and the hazy solution was stirred at 20° C. for 40 min. Meanwhile, a solution of 3-bromo-6-chloro-2-methoxypyridine (1.16 kg, 5.25 mol) in toluene (11 L) was prepared under a nitrogen atmosphere and degassed under reduced pressure. The solution was then cannulated into the reaction mixture. PdCl₂(Xantphos) (67.0 g, 88.6 mmol) was added at once, and the reaction mixture was then heated to 54.6 to 55.3° C., which was maintained overnight. The reaction mixture was subsequently cooled to 15 to 20° C. and quenched with a saturated aqueous solution of ammonium chloride (9 L). The organic phase was isolated and dried over Na₂SO₄. The solvents were finally removed under reduced pressure to afford an orange-brown oil (2.97 kg). Two similar batches were run, affording an additional 6.59 kg.

The crude product was chromatographed in 1.2 to 1.3 kg batches over silica gel (20 kg), eluting with 2:3 EtOAc/heptanes, affording 5.28 kg (88%) of 3-(6-chloro-2-methoxypyridin-3-yl)-1-((S)-1-phenylethyl)piperidin-2-one as a mixture of diastereomers.

Step 7. (R)-3-(6-Chloro-2-methoxypyridin-3-yl)-3-methyl-1-((S)-1-phenylethyl)piperidin-2-one: A 20 L vessel equipped with overhead stirrer, nitrogen inlet, temperature probe, and 1 L dropping funnel was flushed with nitrogen and charged with the 1.57:1 3S/3R diastereomeric mixture of 3-(6-chloro-2-methoxypyridin-3-yl)-1-((S)-1-phenylethyl)piperidin-2-one (603 g, 1.75 mol), THF (8 L), and iodomethane (350 mL, 798 g, 5.62 mol). The resulting orange solution was cooled to −72° C., and a solution of KOt-Bu (325 g, 2.90 mol) in THF (2 L) was added over 20 min., maintaining the internal reaction temperature below −70° C. After complete addition, the hazy, beige mixture was stirred at −71° C. to −70° C. for 30 min. The reaction mixture was then stirred at rt. After 2.5 h a warm water bath was applied to bring the internal temperature from −5° C. to rt. The reaction was stirred for an additional 2 h at 29-34° C., after which it was quenched by addition of a saturated aqueous solution of ammonium chloride (4 L) and water (1 L). The aqueous layer was separated and extracted with EtOAc (2×2 L). The combined organic phases were then washed with brine (3 L), dried over Na₂SO₄, and concentrated under reduced pressure to afford a dark purple-red mass (717 g, impure). The crude product was purified by column chromatography on silica gel (18 Kg), eluting 7:13 EtOAc/heptanes. The desired (R,S) diastereomer eluted after the (R,R) diastereomer and could be identified by TLC (SiO₂, 7:13 EtOAc/heptanes). Fractions containing the pure (R,S) diastereomer were combined, and the solvents were removed under reduced pressure to afford a pink-purple, crystalline solid (415 g, 1.16 mol, 66% yield).

Step 8. (R)-6-Chloro-3-(3-methyl-2-oxopiperidin-3-yl) pyridin-2(1H)-one: In a 10 L flask, (R)-3-(6-chloro-2-methoxypyridin-3-yl)-3-methyl-1-((S)-1-phenylethyl)piperidin-2-one (1.33 kg, 3.70 mol) was stirred under reflux in heptafluorobutyric acid (3.5 L) and anisole (1.2 L) for 4 days. The reaction mixture was then concentrated by batchwise kughelrohr distillation in 2-3 L flasks (ca. 120° C., 10⁻² mbar). To the residue was added a 1:1 mixture of acetone and 2-PrOH until the flask was full. After standing overnight, the mixture could be stirred. Upon formation of a uniform suspension, the crude product was collected by filtration. The filter cake was washed with an acetone/2-PrOH mixture until no color was observed in the eluent, and then it was dried in air. A total of 2.10 kg was prepared using this process and combined for the immediately following purification process.

Water (1.5 L) was added to the 2.10 kg of solid from the process immediately above, followed by an 85% aqueous solution of potassium hydroxide (470 g, ca. 7.1 mol). The workup mixture became hot and a water bath was applied to moderate the exotherm. The workup mixture was stirred by hand until automatic stirring was possible, after which the solution was stirred at rt for 2 h. Activated charcoal (100 g)

was then added, and stirring was continued for 1 h at rt. Undissolved solids were then removed by filtration over a pad of Celite® and washed with an aqueous solution of KOH (50. g in 500 mL of water) and then with water (3×250 mL). The filtrate and washings were combined and extracted with DCM by continuous extraction for 8 days. The aqueous layer was then acidified to pH=1 to 2 using 2 M aqueous HCl (ca. 3 L). The precipitated white solid was collected by filtration over a Buchner filter. The solids were washed with water (3×3.0 L). The wet cake was finally stirred in acetonitrile (4.0 L) for 1 h at rt; the solids were then collected by filtration using a Buchner funnel and washed with acetonitrile (3×1.0 L). Drying afforded a white solid (1.70 kg, 80% pure by LCMS).

A column was prepared with 22 kg silica and eluent (3:3:94 HOAc/1-butanol/DCM). The crude product was applied to the column as a hot (80.0° C.) solution in HOAc (2.0 L) and eluted using 3:3:94 HOAc/1-butanol/DCM (120 L) followed by 1:1:23 HOAc/1-butanol/DCM (60 L) mix and finally by 1:1:8 HOAc/1-butanol/DCM (ca. 150 L) until TLC analysis of the eluent failed to detect the product. Fractions (10 L each) of purity greater than 97% (by LCMS) were combined and concentrated. Residual HOAc, 1-butanol, and BuOAc were removed using a membrane pump and a bath temperature of 65° C. The column was regenerate via elution of 3:3:94 HOAc/1-butanol/DCM (40 L) and an additional batch of crude product (530 g) was similarly purified. A final 530 g batch was purified by similar regeneration and elution of the column. All impure fractions and mother liquors of test batches were combined and purified again under similar conditions.

The combined pure batches (1.50 kg) were stirred in acetone (3.0 L), starting at 60° C. and then cooled to 0° C. The product was collected by filtration, washed with cold acetone (3×1.0 L), and dried to afford Intermediate 1 as a white solid (1.21 kg, ca. 58%). A brown, sticky solid (67 g) was obtained by concentration of the mother liquor. Mixed fractions from the final column were concentrated and combined with this solid to afford 700 g of a brown, sticky solid. Acetone (700 mL) was added, and the resulting mixture was stirred at 60° C. until a uniform slurry was obtained. After further stirring at rt (3 h), the product was collected by filtration and washed with acetone until only a white material remained. After drying in air, an additional 210 g (ca. 10%) of Intermediate 1 was obtained. $^1$H NMR (600 MHz, DMSO-$d_6$) δ 1.41-1.53 (m, 4 H), 1.60-1.69 (m, 1 H), 1.76-1.87 (m, 1 H), 2.21 (td, 1 H), 3.11-3.25 (m, 2 H), 6.83 (br. s., 1 H), 7.36 (br. s., 1H), 7.53 (d, 1 H), 11.84 (br. s., 1 H). LCMS (APCI): m/z: 241.1 [M+H] (100%). $[α]_D^{21}$=−92° (DMF, c=0.50).

The absolute configuration of the (R)-6-chloro-3-(3-methyl-2-oxopiperidin-3-yl)pyridin-2(1H)-one prepared according to this method was established by correlation of its $[α]_D$ measurement to a batch of known chirality prepared by the following method.

Preparation of (R)-6-Chloro-3-(3-methyl-2-oxopiperidin-3-yl)pyridin-2(1H)-one with Confirmation of Chirality Step A. 2-(6-Chloro-2-methoxypyridin-3-yl)propanenitrile: To a suspension of 3-bromo-6-chloro-2-methoxypyridine (99.9 g, 449 mmol), [1,1'-bis(diphenylphosphino)ferrocene]dichloropalladium(II) complex with DCM (2.76 g, 3.38 mmol), and NaOtBu (105 g, 1090 mmol) in dioxane (805 mL) was added tert-butyl cyanoacetate (64.8 mL, 454 mmol) under nitrogen. The reaction mixture was heated for 235 min while maintaining the internal reaction temperature at 75° C. under nitrogen. After being cooled to 20° C., to the reaction mixture was added MeI (55.9 mL, 898 mmol) in one portion, and the resulting mixture was stirred overnight at rt. Celite® (24 g) was added to the reaction mixture, and the resulting mixture was filtered through a 370 g silica plug. The plug was eluted with EtOAc/heptanes (1:3, 2.0 L), and the combined filtrate was concentrated. A solution of the crude residue (133.9 g) in DMSO (330 mL) and water (67 mL) was heated at 130° C. for 15.8 h. The reaction mixture was filtered through a plug of Celite®, and the filter cake was rinsed with MTBE and water. The filtrate was filtered again through a plug of Celite® and the filter cake was washed with MTBE and water. The filtrate was partitioned between MTBE (total volume=2.0 L), water (total volume=1.0 L) and brine (100 mL). The layers were separated and the organic layer was washed with water (1.0 L) and brine (750 mL), dried over $Na_2SO_4$, and concentrated to afford the title compound (87.6 g, 99%) as a dark brown oil, which was used for the next step without any further purification. $^1$H NMR (600 MHz, CDCl$_3$) δ 1.58 (d, 3H), 4.01 (s, 3H), 4.11 (q, 1H), 6.97 (d, 1H), 7.66 (d, 1H). LCMS (ESI) m/z: 197.2 [M+H] (100%).

Step B. (R)-3-(6-chloro-2-methoxypyridin-3-yl)-3-methylpiperidin-2-one: A solution of 2-(6-chloro-2-methoxypyridin-3-yl)propanenitrile (25.9 g, 132 mmol) and tert-butyl 2,2-dioxooxathiazinane-3-carboxylate (45.8 g, 193 mmol) in THF (440 mL), under nitrogen, was cooled in an ice/water bath for 10 min. To this solution was added a solution of KHMDS in THF (1.0 M, 255 mL, 260 mmol) over 25 min, while maintaining internal reaction temperature at or below 20° C. After continued stirring for 15 min and with the cold bath still present, conc. HCl aqueous (91 mL) was added cautiously in one portion, and the resulting mixture was stirred for 10 min. The reaction mixture was then heated to reflux for 2.3 h. Cooling with an ice/water bath was commenced, and, when the internal temperature reached 24° C., the reaction was quenched by portionwise addition of a saturated aqueous solution of ammonia (70 mL). Volatile components were removed under reduced pressure, and the residue was partitioned between EtOAc (1.0 L) and 5% (w/v) aqueous sodium carbonate (600 mL). The aqueous layer was extracted with EtOAc (500 mL), and the combined organic extracts were dried over $Na_2SO_4$ and concentrated under reduced pressure to afford crude residue as a dark red-brown oil (33.84 g). To a solution of the residue (33.3 g) in MeOH (310 mL) was added a 4.5 M aqueous solution of KOH. The reaction was then heated to reflux for 8.5 h. Heating was continued, at this point, with a distillation head for 2.2 h, collecting a total of ca. 175 mL of distillate. Reflux was then resumed for an additional 1.5 h, whereupon it was cooled to rt and concentrated under reduced pressure to remove its low-boiling components. Phosphoric acid (85%, 24 mL) was added to the resulting suspension, and solids were collected by vacuum filtration after thorough mixing. This material was washed with several small portions of water and azeotropically dried by evaporation from MeCN to the title compound as a tan-brown solid (15.3 g, 46%), which was ca. 90% pure. $^1$H NMR (600 MHz, CDCl$_3$) δ 1.58-1.64 (m, 1 H), 1.66 (s, 3 H), 1.76-1.82 (m, 1 H), 1.92-2.01 (m, 1H), 2.26 (td, 1 H), 3.35-3.42 (m, 1 H), 3.47 (td, 1 H), 3.97 (s, 3 H), 5.91 (br. s., 1 H), 6.91 (d, 1 H), 7.53 (d, 1 H).

Two enantiomers of 3-(6-chloro-2-methoxypyridin-3-yl)-3-methylpiperidin-2-one were separated via chiral preparative SFC.

Peak 1

Analytical chiral SFC retention time of 5.679 min (Method: Column: Phenomenex Lux Amylose-2, 4.6 mm×250 mm, 5 µm; Mobile Phase A: $CO_2$, Mobile Phase B: MeOH+0.2% Ammonia; Gradient: Hold 95% A for 1.5 min, then a linear gradient from 95% A to 40% A over 9 min, hold 40% A for 1.0 min, then equilibrate column at 95% A for 1.0 min. Flow: 3 mL/min; Backpressure 120 Bar; Column Temperature: 40° C.; UV detection 210 nm).

Preparative conditions are as follows: Column: Phenomenex Lux Amylose-2 21.2 mm×500 mm, 5 µm; Isocratic mobile phase: 80% $CO_2$: 20% MeOH+0.2% Ammonia; Backpressure: 120 Bar; Flow: 80 mL/min, System temperature 40° C.; UV detection 210 nm.

The absolute configuration of this enantiomer was assigned by X-ray crystallography. The crystal used for the X-ray crystallography was obtained from DCE/heptanes, using the following vapor diffusion procedure: A one dram vial was charged with 20 mg of 6-chloro-2-methoxypyridin-3-yl)-3-methylpiperidin-2-one (Peak 1), and this material was dissolved in minimal dichloroethane (ca. 400 µL) to obtain a homogeneous solution. This open one dram vial was placed inside a 20 mL scintillation vial containing a charge of heptane (ca. 3 mL). The outer vial was sealed, and vapour diffusion was allowed to occur over 5 days. Single crystals were removed from the inner vial with a spatula, rinsed with heptane, and analyzed by X-ray crystallography. FIG. 1 is an ORTEP drawing of (S)-3-(6-chloro-2-methoxy-pyridin-3-yl)-3-methylpiperidin-2-one.

Single Crystal X-Ray Analysis for (S)-3-(6-chloro-2-methoxypyridin-3-yl)-3-methylpiperidin-2-one: Data collection was performed on a Bruker APEX diffractometer at room temperature. The structure was solved by direct methods using SHELX software suite in the space group $P2_1$. The structure was subsequently refined by the full-matrix least squares method. All non-hydrogen atoms were found and refined using anisotropic displacement parameters. The structure was solved with five molecules in the asymmetric unit, with a half-occupied disordered solvate. All hydrogen atoms were placed in calculated positions and were allowed to ride on their carrier atoms. The final refinement included isotropic displacement parameters for all hydrogen atoms. Analysis of the absolute structure using likelihood methods (R. W. W. Hooft et al. *J. Appl. Cryst.* (2008), 41, 96-103) was performed using PLATON (A. L. Spek, *J. Appl. Cryst.* (2003), 36, 7-13). The final R-index was 5.5%. A final difference Fourier revealed no missing or misplaced electron density, aside from a few higher than normal residuals near the half occupied solvate. Pertinent crystal, data collection and refinement of (S)-3-(6-chloro-2-methoxypyridin-3-yl)-3-methylpiperidin-2-one are summarized in Table 1, and graphically presented in FIG. 1.

TABLE 1

Crystal data and structure refinement for
Empirical formula C124 H140 Cl10 N20 O21

| | |
|---|---|
| Formula weight | 2601.06 |
| Temperature | 273(2) K |
| Wavelength | 1.54178 Å |
| Crystal system | Monoclinic |
| Space group | P2(1) |
| Unit cell dimensions | a = 12.4551(9) Å α = 90°. |
| | b = 11.7120(9) Å β = 92.151(3)°. |
| | c = 24.2745(18) Å γ = 90°. |

TABLE 1-continued

Crystal data and structure refinement for
Empirical formula C124 H140 Cl10 N20 O21

| | |
|---|---|
| Volume | 3538.5(5) Å$^3$ |
| Z | 1 |
| Density (calculated) | 1.221 Mg/m$^3$ |

Peak 2 Based on the X-ray analysis of peak 1, which was assigned as (S)-enantiomer, peak 2 was assigned as (R)-enantiomer. Analytical SFC retention time 6.478 min (preparative and analytical methods same as for peak 1 above). $^1$H NMR (600 MHz, CDCl$_3$) δ 1.61-1.63 (m, 1H), 1.67 (s, 3H), 1.77-1.83 (m, 1H), 1.95-2.01 (m, 1H), 2.26 (td, 1H), 3.39-3.41 (m, 1H), 3.48 (td, 1H), 3.88 (s, 3H), 6.06 (br. s., 1H), 6.92 (d, 1H), 7.54 (d, 1H). LCMS (ESI) m/z: 255.0 [M+H] (100%).

Step C. (R)-6-Chloro-3-(3-methyl-2-oxopiperidin-3-yl)pyridin-2(1H)-one: TMSCI (18.0 mL, 51.1 mmol) was added, in one portion, to a light yellow solution of (R)-3-(6-chloro-2-methoxypyridin-3-yl)-3-methylpiperidin-2-one (3.32 g, 13.0 mmol) and sodium iodide (7.68 g, 51.2 mmol) in MeCN (39 mL), causing the immediate formation of a precipitate. The reaction mixture, loosely capped, was then heated in a 35° C. aluminum block for 4 h. After heating for ca. 15 min, the vial was sealed to prevent loss of solvent. After heating was ended, a 0.5 M aqueous solution of sodium thiosulfate (36 mL) was added, and the resulting mixture was partitioned between 3:17 EtOH/DCM and brine (250 mL separation funnel). Much solid remained undissolved, despite dilution of the workup mixture with both 3:17 EtOH/DCM and water (to a combined volume of ca. 500 mL). A light yellow-green solid was removed from the workup mixture by filtration, the layers were separated, and the aqueous layer was further extracted with 3:17 EtOH/DCM (2×). The combined organic layers were dried over Na$_2$SO$_4$ and concentrated to afford a yellow solid. 1:4 EtOH/DCM (ca. 50 mL) was added to this solid, and gentle heat was applied to dissolve as much as possible. The resulting mixture was applied to a 65 g RediSep® silica pre-column and purified by MPLC (80 g RediSep® Rf Gold® silica main column). The solids filtered off of the workup mixture were applied to a second silica pre-column as a suspension in EtOH/DCM and similarly purified by MPLC. Finally, the aqueous layer from the workup was then evaporated, and the resulting solids were applied to a third silica pre-column as a suspension in EtOH/DCM and similarly purified by MPLC. The most pure, colorless fractions from the first two columns were combined and evaporated, and the residue was triturated with EtOAc to afford Intermediate 1 as a white solid (806 mg, 26%). $^1$H NMR (600 MHz, DMSO-d$_6$) δ 1.42-1.53 (m, 4 H), 1.60-1.68 (m, 1 H), 1.76-1.87 (m, 1 H), 2.21 (td, 1 H), 3.11-3.25 (m, 2 H), 6.84 (br. s., 1 H), 7.36 (br. s., 1 H), 7.53 (d, 1 H), 11.80 (br. s., 1 H). $[\alpha]_D^{21}$=−100° (DMF, c=0.30). LCMS data was acquired on a representative chromatography fraction. LCMS (APCI) m/z: 241.0 [M+H] (100%). Fractions containing Intermediate 1 in acceptable purity or with a colored impurity were also combined and evaporated, and the resulting solid was triturated with EtOAc to afford a nearly white solid (398 mg, 13%).

Intermediate 2. 5-Methyl-3-(4,4,5,5-tetramethyl-1,3,2-dioxaborolan-2-yl)quinoline

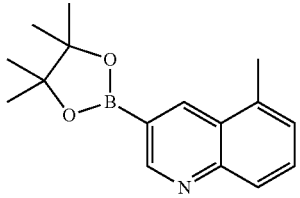 [SMILES: Cc1cccc2ncc(B3OC(C)(C)C(C)(C)O3)cc12]

Step 1. 8-Bromo-5-methylquinoline : A suspension of 2-bromo-5-methylaniline (500 g, 2.69 mol), glycerin (519 g, 5.64 mol), and nitrobenzene (350. g, 2.85 mol) in sulfuric acid (1230 mL, 75%), split into two batches, was stirred at 140° C. for 3 h. After cooling to rt, the two batches were combined and poured into a solution of NaOH (7.5 L, 10 M) in ice-water; the mixture was allowed to stand at rt overnight. The undissolved solids were then collected by filtration and dissolved in EtOAc (10 L). The resulting solution was washed with water (10 L) and brine (10 L), dried over $Na_2SO_4$, and evaporated. The obtained crude product was purified by column chromatography (EtOAc gradient in PE from 0% to 50%) to afford 8-bromo-5-methylquinoline as a white solid (640 g, 52%).

Step 2. 8-Bromo-5-methyl-3-(4,4,5,5-tetramethyl-1,3,2-dioxaborolan-2-yl)quinolone The following reaction was conducted in three batches, and, for each, a suspension of (1,5-cyclooctadiene)(methoxy)iridium(I) dimer (28.4 g, 42.9 mmol) and 4,4'-di-tert-butyl bipyridine (23.0 g, 85.8 mmol) in heptanes (1.6 L) was degassed under vacuum and back-filled with nitrogen (three cycles) and subsequently stirred at 25° C. for 30 min. 8-Bromo-5-methylquinoline (200. g, 858 mmol) and bis(pinacolato)diboron (268 g, 944 mmol) were added, in turn, at 25° C. After the addition, the mixture was degassed under vacuum and back-filled with nitrogen (three cycles). The resulting mixture was then heated to 55° C. for 3 h. The three batches were then combined, cooled to 40° C., and filtered through a pad of Celite®. The filtrate was partitioned between EtOAc (10 L) and water (6.0 L), and the aqueous layer was further extracted with EtOAc (2×5.0 L). The combined organic layers were washed with water (10. L) and brine (10. L), dried over $Na_2SO_4$, and concentrated to afford the crude product. After trituration with 1:20 EtOAc/PE (3.0 L), 8-bromo-5-methyl-3-(4,4,5,5-tetramethyl-1,3,2-dioxaborolan-2-yl)quinoline was obtained as a yellow solid (480 g, 53.6%).

Step 3. 5-Methyl-3-(4,4,5,5-tetramethyl-1,3,2-dioxaborolan-2-yl)quinolone: The following reaction was conducted in twelve batches, and, for each, a mixture of 8-bromo-5-methyl-3-(4,4,5,5-tetramethyl-1,3,2-dioxaborolan-2-yl)quinoline (60.0 g, 172 mmol), $Et_3N$ (26.8 g, 259 mmol) and dry palladium on carbon (6.0 g) in EtOAc (1.0 L) was evacuated and back-filled with hydrogen gas (three cycles) and then pressurized with hydrogen (10 psig) at 25° C. for 1 h. The combined reaction batches were filtered through a pad of Celite®, and the filtrate was concentrated to dryness. PE (1.8 L) was added to the residue, dissolving as much as possible. After removing insoluble material by filtration, the solution was cooled to −65° C., with stirring, for 30 min. The resulting yellow precipitate was collected by filtration. Trituration of the solid in PE at rt afforded Intermediate 2 as a yellow solid (301 g, 54%). $^1$H NMR (400 MHz, $CDCl_3$) δ 1.40 (s, 12 H), 2.74 (s, 3 H), 7.36 (d, 1 H), 7.62 (dd, 1 H), 7.97 (d, 1 H), 8.78 (s, 1 H), 9.19 (d, 1 H). GCMS (EI) m/z: 269 [M$^+$] (81%).

Intermediate 3. 7-Chloro-5-methylquinoline

A 250 mL round bottom flask was charged with XPhos-Pd-G2 (806 mg, 1.02 mmol) and 5,7-dichloroquinoline (4.06 g, 20.5 mmol) and fitted with a reflux condenser. The condenser was sealed with a septum, and the reaction atmosphere was exchanged to nitrogen. Trimethylboroxine (3.85 mL, 27.7 mmol), 1,4-dioxane (68 mL), and aqueous $Na_2CO_3$ (31 mL, 62 mmol, 2.0 M) were added through the condenser. The resulting mixture was heated in a 90° C. aluminum block for 23 h. After cooling, the reaction mixture was diluted with EtOAc, filtered over a small pad of Celite®, and concentrated. The resulting mixture was applied to an 80 g RediSep® Rf Gold® silica column as a solution in toluene and eluted with a gradient of 0 to 50% EtOAc in heptane to afford a 4:1 mixture of title compound and 5-chloro-7-methylquinoline as a white solid (2.93 g, 80%). $^1$H NMR (400 MHz, $CDCl_3$) δ 2.67 (s, 3 H), 7.34-7.37 (m, 1 H), 7.42 (dd, 1 H), 7.96 (d, 1 H), 8.29 (d, 1 H), 8.91 (dd, 1 H). LCMS (ESI) m/z: 178.6 [M+H] (100%).

Intermediate 4. 7-Bromo-5-cyclopropylquinoline

Step 1: A 100 mL flask was charged with 3,5-dibromoaniline (5.00 g, 19.9 mmol), sodium 3-nitrobenzenesulfonate (987 mg, 4.39 mmol), iron(II)sulfate heptahydrate (63.2 mg, 0.658 mmol), and methanesulfonic acid (20 mL). A reflux condenser was added, and the reaction was heated in a 120° C. aluminum block. Glycerol (0.64 mL, 8.8 mmol) was added through the condenser, and the aluminum block temperature was then increased to 130° C. Heating was continued overnight. After cooling to rt, the reaction mixture was diluted with DCM and water, cooled in an ice/water bath, and rendered alkaline by addition of a 50% aqueous solution of NaOH. The resulting mixture was filtered over Celite® and extracted with DCM. The organic phase was dried over $Na_2SO_4$ and concentrated to a brown solid. Purification by chromatography (80 g Si gel, 0-40% EtOAc in heptane gradient over 17 CV and then held at 40%) afforded 5,7-dibromoquinoline as a tan solid (3.19 g, 56%). $^1$H NMR (400 MHz, $CDCl_3$) δ 7.53 (dd, 1 H), 7.96 (d, 1 H), 8.29 (d, 1 H), 8.50 (d, 1 H), 8.93 (dd, 1 H). LCMS (ESI) m/z: 285.9 [M+H] (95%). LCMS data were acquired from the reaction mixture immediately prior to workup.

Step 2: A 20 mL vial was charged with mixture of 5,7-dibromoquinoline (300. mg, 1.05 mmol), Pd(dppf)$Cl_2 \cdot CH_2Cl_2$ (85.4 mg, 0.105 mmol), $Cs_2CO_3$ (188 mg, 3.14 mmol), and potassium cyclopropyltrifluoroborate (186 mg, 1.25 mmol) and sealed with a cap containing a septum. A nitrogen atmosphere was established in the vial, and toluene (6.0 mL) and water (2.0 mL) were added. The reaction mixture was then heated in a 100° C. aluminum block for 19 h. After cooling to rt, the reaction mixture was diluted with EtOAc, filtered through Celite®, dried over $Na_2SO_4$, and concentrated to a brown oil. Purification by MPLC (29 g Si gel, 0-60% EtOAc/heptane gradient) afforded a ca. 2:1 mixture of Intermediate 4 and 5-bromo-7-cyclopropylquinoline as a light yellow oil (88 mg, 34%). $^1$H NMR (400 MHz, $CDCl_3$) δ 0.76-0.81 (m, 2 H), 1.07-1.14 (m, 2 H), 2.29 (tt, 1 H), 7.37-7.39 (m, 1 H), 7.45 (dd, 1 H), 8.14 (d, 1 H), 8.66 (d, 1 H), 8.90 (dd, 1 H). LCMS (ESI) m/z: 248.0 [M+H]

(56%). LCMS data were acquired from the reaction mixture immediately prior to workup.

Intermediate 5. 7-Bromo-5-ethylquinoline

The title compound was prepared in a method analogous to that of 7-bromo-5-cyclopropylquinoline (Intermediate 4), using appropriate starting materials. A ca. 4:1 mixture of Intermediate 5 and 5-bromo-7-ethylquinoline were obtained as a light yellow oil. $^1$H NMR (400 MHz, CDCl$_3$) δ 1.36 (t, 3 H), 3.06 (q, 2 H), 7.42 (dd, 1 H), 7.49 (d, 1 H), 8.15 (d, 1 H), 8.32 (d, 1 H), 8.89 (dd, 1 H). LCMS (APCI) m/z: 236.0 [M+H] (100%). LCMS data were acquired from the reaction mixture immediately prior to workup.

Intermediate 6. 7-Bromo-5-chloroquinoline

The title compound was prepared in a method analogous to that of 5,7-dibromoquinoline (Step 1, Intermediate 4), using appropriate starting materials. A ca. 1:1 mixture of the title compound and 5-bromo-7-chloroquinoline (750 mg, 64%) were obtained as an off-white solid. The title compound could also be obtained as a single regioisomer by SFC purification using the following method: Chiral Tech AD-H 250×21.2 mm, 5 μm particle size; 1:4 MeOH/CO$_2$ eluent; 120 bar backpressure; 80.0 mL/min. flow rate. Fractions containing the later-eluting peak were combined and evaporated to afford Intermediate 6 (115 mg, 9.8%) as a single regioisomer. $^1$H NMR (400 MHz, CDCl$_3$) δ 7.53 (dd, 1 H), 7.76 (d, 1 H), 8.23 (d, 1 H), 8.53 (d, 1 H), 8.96 (dd, 1 H). LCMS (ESI) m/z: 241.9 [M+H] (96%).

Intermediate 7. 7-Chloro-5-fluoroquinoline

The title compound was prepared in a method analogous to that of 5,7-dibromoquinoline (Step 1, Intermediate 4), using appropriate starting materials and a 150° C. reaction temperature. After chromatography, a ca. 9:1 mixture of Intermediate 7 and 5-chloro-7-fluoroquinoline was obtained as an off-white solid. $^1$H NMR (400 MHz, CDCl$_3$) δ 7.23 (dd, 1 H), 7.45 (dd, 1 H), 7.92 (s, 1 H), 8.37 (dd, 1 H), 8.95 (dd, 1 H). GCMS (EI) m/z: 181 [M$^+$] (100%). GCMS data were acquired from the reaction mixture immediately prior to workup.

Intermediate 8 (R)-3-(6-Chloro-2-methoxypyridin-3-yl)-3-methylpyrrolidin-2-one

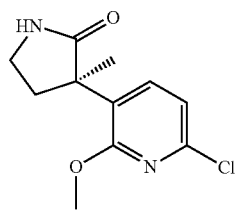 [SMILES: COc1nc(Cl)ccc1[C@@]1(C)CCNC1=O]

Step 1. Methyl 2-(6-chloro-2-methoxypyridin-3-yl)propanoate: To a dry flask was added 3-bromo-6-chloro-2-methoxypyridine (9.7 g, 43.7 mmol), palladium(0)bis(dibenzylideneacetone) (1.3 g, 2.2 mmol), and zinc fluoride (3.4 g, 32.7 mmol). The mixture was degassed with nitrogen. A solution of tri-tert-butylphoshine/toluene (1.0 M, 4.4 mL, 4.4 mmol) in DMF (146 mL) was then added to the degassed mixture. After stirring, (E)-(1-methoxyprop-1-enyloxy)trimethylsilane (15.2 mL, 65 mmol) was added and the reaction was heated at 85° C. for 18 h. The mixture was partitioned between MTBE and brine. The aqueous layer was extracted with MTBE. The combined organic layers were dried over Na$_2$SO$_4$ and concentrated. Purification by silica gel column chromatography (330 g RediSep® Rf Gold® column, 30 to 65% DCM in heptanes) provided methyl 2-(6-chloro-2-methoxypyridin-3-yl)propanoate (6.4 g, 64%); $^1$H NMR (600 MHz, CDCl$_3$) δ: 1.44 (d, 3H), 3.67 (s, 3H), 3.91 (q, 1H), 3.95 (s, 3H), 6.89 (d, 1H), 7.45 (d, 1H).

Step 2. Methyl 2-(6-chloro-2-methoxypyridin-3-yl)-3-cyano-2-methylpropanoate: In a dry flask containing lithium bis(trimethylsilyl)amide/toluene (1.0 M, 13.1 mL, 13.1 mmol) and THF (18 mL) at −78° C. was added methyl 2-(6-chloro-2-methoxypyridin-3-yl)propanoate (2.39 g, 10.4 mmol) dropwise via syringe over 12 min resulting in a bright yellow solution. After 40 min, the resulting solution was added dropwise to a dry flask containing a solution of 2-bromoacetonitrile (1.38 mL, 20.8 mmol) in THF (18 mL) at 0° C. over 15 min, resulting in a color change from colorless to yellow to dark red-brown. Additional THF (2×1.5 mL) was used to complete the transfer. After 50 min, the reaction was quenched with saturated aqueous ammonium chloride (18 mL). The mixture was diluted with heptanes (4× the reaction volume). The aqueous layer was extracted with 1:1 EtOAc/heptanes (2×200 mL). The combined organic layers were dried over Na$_2$SO$_4$ and concentrated. Purification by silica gel column chromatography (220 g RediSep® Rf Gold® column, 5 to 18% EtOAc in heptanes) provided methyl 2-(6-chloro-2-methoxypyridin-3-yl)-3-cyano-2-methylpropanoate (2.35 g, 84%) as a white solid. $^1$H NMR (600 MHz, CDCl$_3$) δ: 1.74 (s, 3H), 3.07 (d, 1H), 3.14 (d, 1H), 3.67 (s, 3H), 3.95 (s, 3H), 7.00 (d, 1H), 7.57 (d, 1H); MS (AP+)(M+H) 269.

Step 3. 3-(6-Chloro-2-methoxypyridin-3-yl)-3-methylpyrrolidin-2-one: A Parr bottle was charged with a solution of methyl 2-(6-chloro-2-methoxypyridin-3-yl)-3-cyano-2-methylpropanoate (2.35 g, 8.73 mmol) in 7 M ammonia in MeOH and a slurry of Raney nickel (5.82 g, 67.9 mmol, washed 2× with water and 4× with MeOH) in 7 M ammonia in MeOH (99 mL total to charge both reagents, 690 mmol). The reaction was shaken with hydrogen (30 psi) for 6 h. The catalyst was filtered through a pad of Celite® under nitrogen rinsing with ethanol. The filtrate was then concentrated to give a light green oil/foam. Purification by silica gel column chromatography (80 g RediSep® column, 30 to 100% Ethyl acetate in Heptanes) provided 3-(6-chloro-2-methoxypyridin-3-yl)-3-methylpyrrolidin-2-one (1.9 g, 90%) as a white solid. $^1$H NMR (600 MHz, CDCl$_3$) δ: 1.56 (s, 3H), 2.08 (ddd, 1H), 2.58 (dt, 1H), 3.37 (td, 1H), 3.40-3.46 (m, 1H), 3.97 (s, 3H), 5.86 (br. s., 1H), 6.89 (d, 1H), 7.61 (d, 1H); MS (ES+)(M+H) 241.

This intermediate can also be prepared according to procedures presented in PCT Patent Application Number PCT/IB2014/064836.

The racemate was separated via preparative SFC.

Peak 1: (S)-3-(6-chloro-2-methoxypyridin-3-yl)-3-methylpyrrolidin-2-one

Analytical chiral SFC retention time of 5.392 min (Method: Column: Phenomenex Lux Amylose-2, 4.6 mm×250 mm, 5 μm; Mobile Phase A: CO$_2$, Mobile Phase B: MeOH; Gradient: Hold 95% A for 1.5 min, then a linear gradient from 95% A to 40% A over 9 min, hold 40% A for 1.0 min, then equilibrate column at 95% A for 1.0 min. Flow: 3 mL/min; Backpressure 120 Bar; Column Temperature: 40° C.; UV detection 210 nm).

Preparative conditions are as follows: Column: Phenomenex Lux Amylose-2 21.2 mm×500 mm, 5 μm; Isocratic mobile phase: 80% CO$_2$:20% MeOH; Backpressure: 120 Bar; Flow: 80 mL/min, System temperature 40° C.; UV detection 210 nm.

Based on the X-ray analysis of (R)-3-(2-methoxy-6-(1-methyl-1H-indol-5-yl)pyridin-3-yl)-3-methylpyrrolidin-2-one, which was derived from peak 2, peak 1 was assigned as (S)-enantiomer.

Peak 2: (R)-3-(6-chloro-2-methoxypyridin-3-yl)-3-methylpyrrolidin-2-one

Chiral SFC retention time 5.94 min (same method as peak 1 above). Further purification, if necessary, could be accomplished by silica gel column chromatography (0-2% MeOH/DCM) followed by preparative HPLC. Based on the X-ray analysis, Peak 2 was assigned as (R)-3-(2-methoxy-6-(1-methyl-1H-indol-5-yl)pyridin-3-yl)-3-methylpyrrolidin-2-one, which was derived from Peak 2, peak 2 was assigned as the (R)-enantiomer.

(R)-3-(6-Chloro-2-methoxypyridin-3-yl)-3-methylpyrrolidin-2-one was derivatized, and single crystal x-ray diffraction was used to establish its absolute stereochemistry.

Preparation and Confirmation of Chirality of (R)-3-(2-Methoxy-6-(1-methyl-1H-indol-5-yl)pyridin-3-yl)-3-methylpyrrolidin-2-one

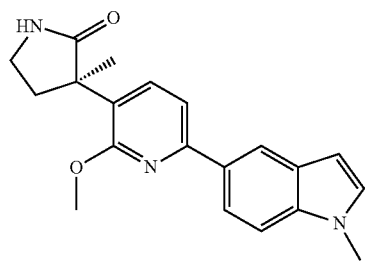 [SMILES: COc1nc(-c2ccc3c(ccn3C)c2)ccc1[C@@]1(C)CCNC1=O]

Figure 2:
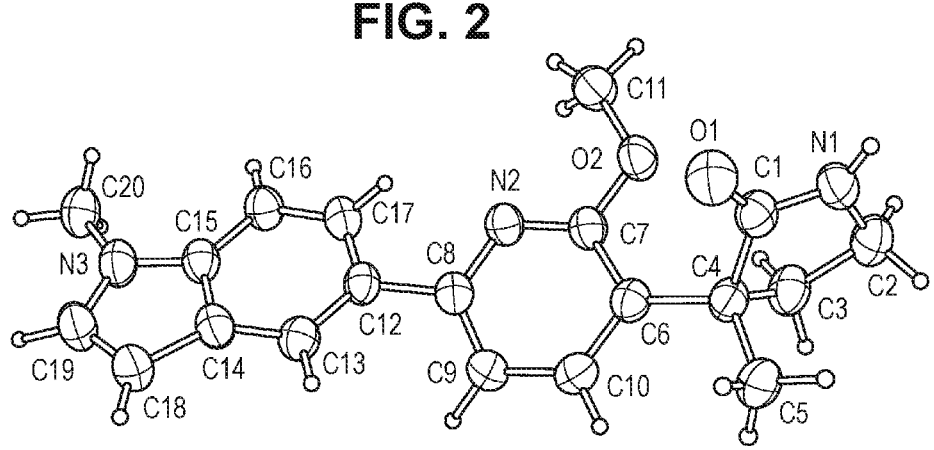
FIG. 2 is a X-ray crystal structure (ORTEP drawing) of (R)-3-(2-methoxy-6-(1-methyl-1H-indol-5-yl)pyridin-3-yl)-3-methylpyrrolidin-2-one.

To a vial was added (R)-3-(6-chloro-2-methoxypyridin-3-yl)-3-methylpyrrolidin-2-one (56.6 mg, 0.24 mmol) which was evaporated with dioxane (2.0 mL). 1-methyl-1H-indol-5-ylboronic acid (63.4 mg, 0.36 mmol) was next added followed by Pd(dppf)Cl$_2$ (7.5 mg, 0.01 mmol). The mixture was sealed and degassed with nitrogen. Degassed dioxane (1.9 mL) and degassed 2 M Na$_2$CO$_3$ (0.27 mL, 2.3 equiv) were then added to the solid mixture. The reaction was stirred for 16 h at 110° C. The reaction was concentrated and partitioned between EtOAc and 10% (w/v) aqueous Na$_2$CO$_3$. The organic layer was washed with brine, dried over Na$_2$SO$_4$, and concentrated to provide a crude brown glass. Purification by column chromatography (4 g Redisep® Rf Gold® column) with a 40 to 100% EtOAc/heptane gradient provided (R)-3-(2-methoxy-6-(1-methyl-1H-indol-5-yl)pyridin-3-yl)-3-methylpyrrolidin-2-one (78 mg, 99%) as a pale yellow glass. $^1$H NMR (600 MHz, CDCl$_3$) δ: 1.62 (s, 3H), 2.10 (ddd, 1H), 2.67-2.76 (m, 1H), 3.37-3.47 (m, 2H), 3.82 (s, 3H), 4.10-4.12 (m, 3H), 5.59 (br. s., 1H), 6.56 (d, 1H), 7.07 (d, 1H), 7.34-7.39 (m, 2H), 7.67 (d, 1H), 7.92-7.96 (m, 1H), 8.30 (s, 1H); MS (AP+)(M+H) 336. The absolute stereochemistry was obtained via X-ray crystallographic analysis of single crystals obtained via crystallization from a mixture of DCM and EtOH. FIG. 2 is an ORTEP drawing of (R)-3-(2-methoxy-6-(1-methyl-1H-indol-5-yl)pyridin-3-yl)-3-methylpyrrolidin-2-one.

Single Crystal X-Ray Analysis for (R)-3-(2-methoxy-6-(1-methyl-1H-indol-5-yl)pyridin-3-yl)-3-methylpyrrolidin-2-one:

Data collection was performed on a Bruker APEX diffractometer at rt

The structure was solved by direct methods using SHELX software suite in the space group P2$_1$2$_1$2$_1$. The structure was subsequently refined by the full-matrix least squares method. The hydrogen atoms located on nitrogen were found from the Fourier difference map and refined with distances restrained. The remaining hydrogen atoms were placed in calculated positions and were allowed to ride on their carrier atoms. The final refinement included isotropic displacement parameters for all hydrogen atoms.

The analysis of the absolute structure using likelihood methods (R. W. W. Hooft et al. *J. Appl. Cryst.* (2008), 41, 96-103) was performed using PLATON (A. L. Spek, *J. Appl. Cryst.* (2003), 36, 7-13.). The results indicate that the absolute structure has been correctly assigned. The method calculates that the probability that the structure is correct is 100.0. The Hooft parameter is reported as 0.020 with an esd of 0.07. The final R-index was 3.1%. A final difference Fourier revealed no missing or misplaced electron density. Pertinent crystal, data collection and refinement of (R)-3-(2-methoxy-6-(1-methyl-1H-indol-5-yl)pyridin-3-yl)-3-methylpyrrolidin-2-one are summarized in Table 2, and graphically presented in FIG. 2.

TABLE 2

| Crystal data and structure refinement for Empirical formula C20 H21 N3 O2 | |
|---|---|
| Formula weight | 335.40 |
| Temperature | 298(2) K |
| Wavelength | 1.54178 Å |
| Crystal system | Orthorhombic |
| Space group | P2(1)2(1)2(1) |
| Unit cell dimensions | a = 7.5866(7) Å α = 90°. |
| | b = 13.5045(11) Å β = 90°. |
| | c = 16.7586(14) Å γ = 90°. |
| Volume | 1717.0(3) Å3 |
| Z | 4 |
| Density (calculated) | 1.297 Mg/m$^3$ |

EXAMPLES

Example 1

(R)-3-(3-Methyl-2-oxopiperidin-3-yl)-6-(5-methylquinolin-3-yl)pyridin-2(1H)-one; tautomer (R)-3-(2-hydroxy-6-(5-methylquinolin-3-yl)pyridin-3-yl)-3-methylpiperidin-2-one

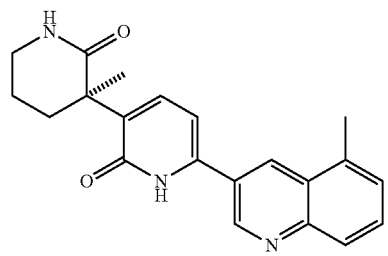 [SMILES: Cc1cccc2ncc(-c3ccc([C@@]4(C)CCCNC4=O)c(=O)[nH]3)cc12]

A 1 L flask was charged with (R)-6-chloro-3-(3-methyl-2-oxopiperidin-3-yl)pyridin-2(1H)-one (32.0 g, 133 mmol), 5-methyl-3-(4,4,5,5-tetramethyl-1,3,2-dioxaborolan-2-yl) quinoline (42.8 g, 159 mmol), sodium bicarbonate (44.8 g, 533 mmol), and PdCl$_2$(dppf).CH$_2$Cl$_2$ (3.86 g, 4.73 mmol). Freshly degassed 1-propanol (449 mL) was added under air. The reaction flask was quickly fitted with a reflux condenser and a nitrogen/high vacuum line. Magnetic stirring was set at 500 rpm, and the reaction apparatus was repeatedly evacuated and back-filled with nitrogen. The reaction mixture was then heated in a 110° C. aluminum block (at reflux) for 20 h. The reaction mixture slowly darkened and thickened; the rate of stirring was increased to 600 rpm. The reflux condenser was then replaced with a distillation head, and the aluminum block temperature was increased to 130° C. The distillation was discontinued after 1 h, by which time 225 mL of solvent had been removed. After cooling to ca. rt, the reaction mixture was transferred to a 2 L separatory funnel, and DCM (595 mL), water (560 mL), and brine (225 mL) were added. The mixture was then shaken vigorously, and the aqueous layer was further extracted with DCM (once with 500 mL and then with 200 mL). The combined organic phases were dried over sodium sulfate and evaporated (evaporator bath at 50° C.) to afford a dark brown foam/taffy mixture (74.8 g, impure). 2-Propanol (280 mL) was added, and the resulting heterogeneous mixture was heated in a 70° C. aluminum block for 16.5 h. At this point, the re-pulp mixture was a uniform, very thick, fine suspension. After stirring at rt for 3.5 h, the solids were collected by vacuum filtration. Additional 2-propanol (74 mL) was used to complete the transfer and rinse the filter cake, which was dried under suction to afford a dark grey solid (46.6 g). SiliCycle's SiliaMetS Thiol resin (25.7 g, 1.23 mmol/g) and 1:4 EtOH/DCM (310 mL) were added to this solid, and the resulting mixture was heated under reflux in a 50° C. aluminum block for 67 h. Because a significant amount of solvent had evaporated, additional DCM (100 mL) was added, and the hot mixture was filtered through Celite® to remove the resin. 1:4 EtOH/DCM (100 mL) was used to complete the transfer and rinse the filter cake. Additional SiliaMetS Thiol resin (25.65 g) was added to the filtrate, and reflux was continued for 23 h. The resin was removed by hot filtration through Celite®, and 1:4 EtOH/DCM (100 mL) was again used to complete the transfer and wash the filter cake. Evaporation of the filtrate afforded a light tan solid (46.8 g, 89% as a mono-EtOH solvate). Deionized water (250 mL) was then added to the solid, and the resulting suspension was subjected to vigorous stirring at rt for 16 h. The undissolved solids were collected by vacuum filtration, and additional deionized water (200 mL) was used to complete the transfer and wash the filter cake. After drying under suction and then in air for several days, the product, still wet, weighed 67.8 g.

Isolation as a mono-ethanol solvate, free base solid form. As noted in the immediately preceding paragraph, the title compound was isolated as a mono-ethanol solvate by evaporation of a solution of high HPLC purity and low Pd content (R)-3-(3-methyl-2-oxopiperidin-3-yl)-6-(5-methylquinolin-3-yl)pyridin-2(1H)-one from 1:4 EtOH/DCM (25.67 g solute in 310 mL of solvent) or 1:9 EtOH/DCM solution (7.92 g solute in 100 mL of solvent). $^1$H NMR (600 MHz, DMSO-d$_6$) δ 1.05 (t, 3 H), 1.39-1.47 (m, 1 H), 1.48 (s, 3 H), 1.65-1.73 (m, 1 H), 1.79-1.90 (m, 1 H), 2.38 (td, 1 H), 2.75 (s, 3 H), 3.12-3.20 (m, 1 H), 3.31 (td, 1 H), 3.44 (q, 2 H), 6.24 (s, 1 H), 6.84 (d, 1 H), 7.29 (d, 1 H), 7.46 (d, 1 H), 7.50 (d, 1 H), 7.69 (t, 1 H), 7.89 (d, 1 H), 8.79 (s, 1 H), 9.22 (s, 1 H), 12.09 (br. s., 1 H).

Conversion to a monohydrate, free base solid form. Various samples, similarly prepared, of high HPLC purity and low Pd content, including mono-ethanol solvate (28.8 g), water-wet (67.8 g), and mixed ethanol solvate/hydrate (1.46 g) were combined. EtOH (350 mL) and water (90 mL) were added, and the resulting suspension was heated in a 60° C. aluminum block with vigorous stirring for 18 h. After stirring at rt for 4.5 h, the solids were collected by vacuum filtration, and 4:1 EtOH/water (ca. 80 mL) was used to complete the transfer and rinse the filter cake. A cream-colored solid (65.8 g, a mixed EtOH solvate/hydrate form) was obtained after extended drying under suction. This solid was then suspended in a mixture of acetone (250 mL, reagent grade) and water (25 mL, deionized), and the resulting mixture was stirred in a 55° C. aluminum block under a reflux condenser for 18 h. After further stirring at rt (3.5 h), the solids were collected by vacuum filtration. Additional 10:1 acetone/water (40. mL) was used to complete the transfer and rinse the filter cake. Suction was continued overnight to afford Example 1 as a monohydrate (59.9 g, cream-colored solid). $^1$H NMR (600 MHz, DMSO-d$_6$) δ 1.40-1.47 (m, 1 H), 1.48 (s, 3 H), 1.65-1.73 (m, 1 H), 1.79-1.90 (m, 1 H), 2.38 (td, 1 H), 2.75 (s, 3 H), 3.12-3.20 (m, 1 H), 3.27-3.36 (m, 1 H), 6.83 (br. s., 1 H), 7.28 (d, 1 H), 7.46 (d, 1 H), 7.50 (d, 1 H), 7.70 (t, 1 H), 7.89 (d, 1 H), 8.79 (s, 1 H), 9.21 (br. s., 1 H), 12.04 (br. s., 1 H). LCMS (APCI) m/z: 348.1 [M+H] (100%). $^{13}$C NMR (151 MHz, DMSO-d$_6$) δ 18.2 (s, 1C), 19.9 (s, 1C), 23.5 (s, 1C), 33.1 (s, 1C), 41.6 (s, 1C), 43.9 (s, 1C), 104.6 (s, 1C), 125.9 (s, 1C), 126.2 (s, 1C), 126.8 (s, 1C), 127.5 (s, 1C), 130.0 (s, 1C), 130.4 (s, 1C), 135.5 (s, 1C), 135.9 (s, 1C), 136.7 (s, 1C), 141.8 (s, 1C), 147.7 (s, 1C), 148.1 (s, 1C), 161.8 (s, 1C), 174.4 (s, 1C). Anal. Calcd for C$_{21}$H$_{21}$N$_3$O$_2$.H$_2$O: C, 69.02; H, 6.34; N, 11.50. Found: C, 68.99; H, 6.41; N, 11.43. mp 185-187° C. %). [α]$_D^{21}$=−902° (CHCl$_3$, c=0.695).

Powder X-ray diffraction analysis was conducted using a Bruker AXS D4 Endeavor diffractometer equipped with a Cu radiation source. The divergence slit was set at 0.6 mm while the secondary optics used variable slits. Diffracted radiation was detected by a PSD-Lynx Eye detector. The X-ray tube voltage and amperage were set to 40 kV and 40 mA respectively. Data was collected in the Theta-2Theta goniometer at the Cu wavelength Kα$_i$=1.54056 Å from 3.0 to 40.0 degrees 2-Theta using a step size of 0.020 degrees and a step time of 0.3 second. Samples were prepared by placing them in a silicon low background sample holder and rotated during collection. Data were collected using Bruker DIFFRAC Plus software and analysis was performed by EVA diffract plus software.

PXRD data file was not processed prior to peak searching. Using the peak search algorithm in the EVA software, peaks were selected with a threshold value of 1 and a width value of 0.3 were used to make preliminary peak assignments. The output of automated assignments was visually checked to ensure validity and adjustments manually made if necessary. Peaks with relative intensity of 3% were generally chosen. The peaks which were not resolved or were consistent with noise were also discarded. A typical error associated with the peak position from PXRD stated in USP and JP is up to +/−0.2°. For characteristic peaks provided herein, the characteristic peak positions were selected based on visual observation of peak shape and intensity and said positions are +/−0.2°.

Figure 3:
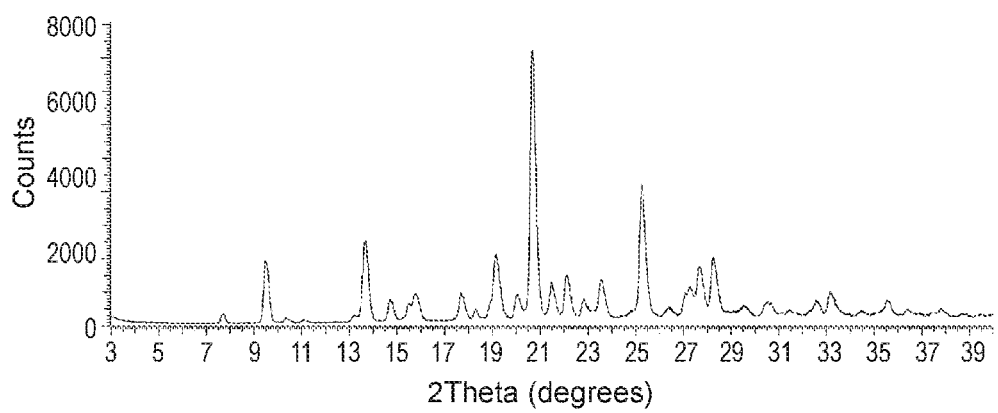
FIG. 3 is the PXRD pattern of crystalline monohydrate form of Example 1.

The PXRD pattern of crystalline monohydrate form of Example 1 is provided in FIG. 3. Characteristic peaks for the crystalline monohydrate of Example 1 include Angle 2θ(°) values of about 9.5, 13.7, 19.2, 20.7, and 25.3. Yet another embodiment of said monohydrate of Example 1 is where characteristic peaks include Angle 2θ(°) values of about 7.7, 9.5, 13.7, 20.7, and 25.3. Yet another embodiment of said monohydrate of Example 1 is where characteristic peaks include Angle 2θ(°) values of about 9.5, 13.7, 19.2, 20.7, 22.1, 23.6, 25.3, and 28.3.

TABLE 3

PXRD peak list for crystalline monohydrate form of Example 1

| Angle 2Θ (°)* | Intensity (%) |
|---|---|
| 7.7 | 3 |
| 9.5 | 23 |
| 13.7 | 30 |
| 14.7 | 7 |
| 15.5 | 6 |
| 15.8 | 10 |
| 17.7 | 9 |
| 18.3 | 3 |
| 19.2 | 23 |
| 20.1 | 8 |
| 20.7 | 100 |
| 21.5 | 12 |
| 22.1 | 15 |
| 22.8 | 6 |
| 23.6 | 14 |
| 25.3 | 49 |
| 26.4 | 3 |
| 27.3 | 11 |
| 27.7 | 18 |
| 28.3 | 21 |
| 29.6 | 3 |
| 30.6 | 5 |
| 32.6 | 5 |
| 33.2 | 8 |
| 35.6 | 5 |
| 37.8 | 3 |

*Values provided are +/−0.2°.

Conversion to a hydrochloride salt solid form. The water-wet sample (289 mg) was dissolved in THF (12 mL), with gentle heating, to afford a clear, light yellow solution. While still hot, and under vigorous stirring, 2.0 M aqueous HCl (0.44 mL) was added. The solution immediately became bright yellow, and a precipitate appeared. After continued stirring at rt for 25 min., the solids were collected by vacuum filtration. EtOAc was used to help complete the transfer and rinse the filter cake. After drying under high vacuum for 21 h, a hydrochloride salt of Example 1 was obtained as a bright yellow solid (209 mg). $^1$H NMR (600 MHz, DMSO-d$_6$) δ 1.41-1.49 (m, 1 H), 1.49 (s, 3 H), 1.65-1.74 (m, 1 H), 1.80-1.91 (m, 1 H), 2.37 (td, 1 H), 2.81 (s, 3 H), 3.12-3.22 (m, 1 H), 3.31 (td, 1 H), 6.98 (br. s., 1 H), 7.33 (br. s., 1 H), 7.51 (d, 1 H), 7.65 (d, 1 H), 7.85 (t, 1 H), 8.06 (d, 1 H), 9.10 (br. s., 1 H), 9.42 (br. s., 1 H), 12.11 (br. s., 1 H). mp 287-298° C. (dec). Anal. Calcd for C$_{21}$H$_{21}$N$_3$O$_2$. HCl: C, 65.71; H, 5.78; N, 10.95; Cl, 9.23. Found: C, 65.26; H, 5.76; N, 10.80; Cl, 9.70.

Figure 4:
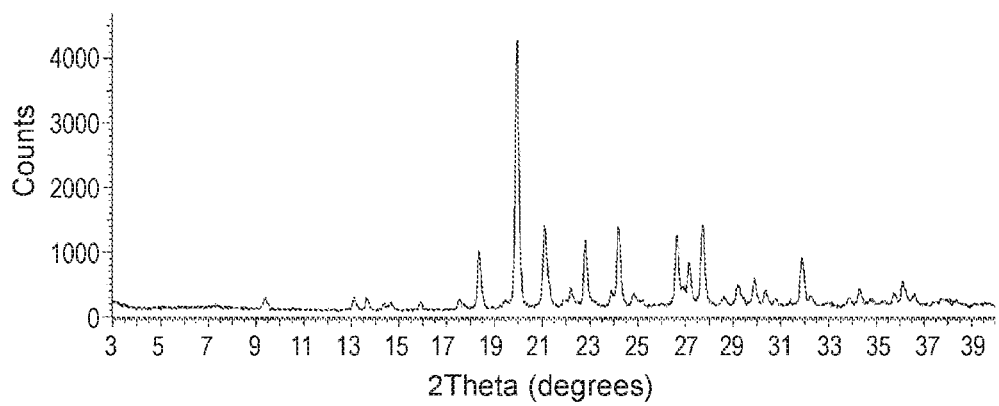
FIG. 4 is the PXRD pattern of crystalline hydrochloride salt of Example 1.

The PXRD pattern of crystalline hydrochloride salt of Example 1 is provided in FIG. 4. Characteristic peaks for the crystalline HCl salt of Example 1 include Angle 2θ(°) values of about 18.4, 20.0, 21.1, 22.8, and 27.7. Yet another embodiment of said HCl salt of Example 1 is where characteristic peaks include Angle 2θ(°) values of about 9.4, 13.1, 13.7, 18.4, 20.0, and 21.1. Yet another embodiment of said HCl salt of Example 1 is where characteristic peaks include Angle 2θ(°) values of about 18.4, 20.0, 21.1, 22.8, 24.2, 26.7, 27.7, and 31.9.

TABLE 4

PXRD peak list for crystalline hydrochloride salt of Example 1

| Angle 2Θ (°)* | Intensity (%) |
|---|---|
| 9.4 | 4 |
| 13.1 | 4 |
| 13.7 | 4 |
| 15.9 | 3 |
| 17.5 | 4 |
| 18.4 | 21 |
| 20.0 | 100 |
| 21.1 | 29 |
| 22.2 | 6 |
| 22.8 | 24 |
| 23.9 | 5 |
| 24.2 | 28 |
| 24.9 | 5 |
| 26.7 | 26 |
| 26.9 | 6 |
| 27.2 | 16 |
| 27.7 | 30 |
| 28.6 | 3 |
| 29.2 | 7 |
| 29.9 | 10 |
| 30.4 | 5 |
| 31.9 | 16 |
| 32.2 | 4 |
| 33.9 | 3 |
| 34.3 | 6 |
| 35.8 | 4 |
| 36.1 | 7 |
| 36.6 | 4 |

*Values provided are +/−0.2°.

Example 2

(R)-3-(3-Methyl-2-oxopiperidin-3-yl)-6-(5-methylquinolin-7-yl)pyridin-2(1H)-one; tautomer (R)-3-(2-hydroxy-6-(5-methylquinolin-7-yl)pyridin-3-yl)-3-methylpiperidin-2-one

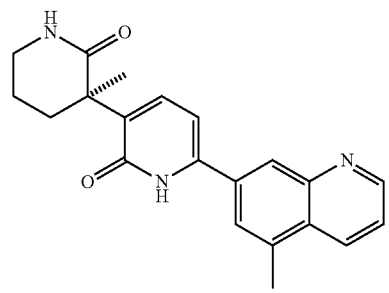 [SMILES: Cc1cc(-c2ccc([C@@]3(C)CCCNC3=O)c(=O)[nH]2)cc2ncccc12]

Step 1: A 250 mL round bottom flask, loaded with XPhos-Pd-G2 (649 mg, 0.825 mmol), bis(pinacolato)diboron (4.61 g, 18.1 mmol), potassium acetate (4.86 g, 49.5 mmol), and 7-chloro-5-methylquinoline (2.93 g, 16.5 mmol, as a 4:1 mixture with 5-chloro-7-methylquinoline), was fitted with a reflux condenser and sealed with a rubber septum. After exchanging the reaction atmosphere to nitrogen, 1,4-dioxane (82 mL) was added, and the flask was heated in a 90° C. aluminum block for 26 h. The reaction mixture was diluted with EtOAc, and the resulting mixture was filtered through Celite®, washed with water, dried over Na$_2$SO$_4$, and evaporated to afford 5-methyl-7-(4,4,5,5-tetramethyl-1,3,2-dioxaborolan-2-yl)quinoline as a light yellow oil, which was used in the next step without purification.

¹H NMR (400 MHz, CDCl₃) δ 1.39 (s, 12 H), 2.69 (s, 3 H), 7.46 (dd, 1 H), 7.75 (s, 1 H), 8.36 (d, 1 H), 8.49 (s, 1 H), 8.95 (dd, 1 H). GCMS (EI) m/z: 269 [M⁺] (86%).

Step 2: A 250 mL round bottom flask was loaded with Pd(OAc)₂ (184 mg, 0.817 mmol), di(1-adamantyl)-n-butylphosphine (352 mg, 0.981 mmol), (R)-6-chloro-3-(3-methyl-2-oxopiperidin-3-yl)pyridin-2(1H)-one (5.12 g, 21.3 mmol), NaHCO₃ (6.87 g, 81.7 mmol) and sealed with a rubber septum. The reaction atmosphere was exchanged to nitrogen, and a solution of 5-methyl-7-(4,4,5,5-tetramethyl-1,3,2-dioxaborolan-2-yl)quinoline (entire sample prepared in the previous step, assumed to be 16.5 mmol for the purpose of stoichiometry calculations) in DMF (65 mL) was added. Overnight heating (100° C. aluminum block) was commenced, and the aluminum block temperature was increased to 110° C. on the following day. Several hours later, the reaction mixture was cooled to rt and filtered through Celite®. The filtrate was partitioned between pH 7 buffer and 1:9 EtOH/DCM, and the organic layer was dried over Na₂SO₄ and concentrated. The residue was applied to a silica pre-column using 1:9 EtOH/DCM and eluted through a 120 g RediSep® Rf Gold® silica column (gradient: 0 to 75% EtOH in DCM) to afford a white solid (5.40 g). EtOAc (30. mL) was added to this solid, and the resulting mixture was temporarily heated using a heat gun. Then, the mixture was allowed to stir overnight, slowly cooling to rt. The undissolved fine, white solid (1.65 g) was collected by filtration. This solid was dissolved in boiling MeOH (ca. 35 mL) and allowed to slowly cool. After reaching rt, the mixture was moved to an ice bath for 2 h and then stored in a −30° C. freezer overnight. Filtration thus afforded Example 2 (single regioisomer) as a white solid (663 mg, 12% over 2 steps). ¹H NMR (400 MHz, CD₃OD) δ 1.54-1.62 (m, 1 H), 1.63 (s, 3 H), 1.77-1.88 (m, 1 H), 1.95-2.10 (m, 1 H), 2.43 (td, 1 H), 2.79 (s, 3 H), 3.30-3.37 (m, 1 H), 3.52 (td, 1 H), 6.78 (d, 1 H), 7.62 (dd, 1 H), 7.67 (d, 1 H), 7.75 (s, 1 H), 8.15 (s, 1 H), 8.58 (d, 1 H), 8.91 (dd, 1 H). HPLC $t_R$ (Method B): 5.24 min. LCMS (ESI) m/z: 348.4 [M+H] (100%).

Example 3

(R)-6-(5-Ethylquinolin-7-yl)-3-(3-methyl-2-oxopiperidin-3-yl)pyridin-2(1H)-one; tautomer (R)-3-(6-(5-ethylquinolin-7-yl)-2-hydroxypyridin-3-yl)-3-methylpiperidin-2-one

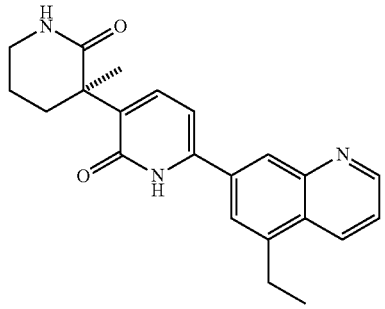 [SMILES: CCc1cc(-c2ccc([C@@]3(C)CCCNC3=O)c(=O)[nH]2)cc2ncccc12]

A 2-5 mL microwave vial was charged with PdCl₂(dppf).CH₂Cl₂ (13.5 mg, 0.0165 mmol), bis(pinacolato)diboron (129 mg, 0.508 mmol), and potassium acetate (136 mg, 1.38 mmol). The vial was then sealed, and its atmosphere was exchanged to nitrogen. A solution of 7-bromo-5-ethylquinoline (109.0 mg, 0.462 mmol, also containing a minor regioisomer) in 1,4-dioxane (3.1 mL) was added through the septum, and the vial was heated in a 105° C. aluminum block. After 1.5 h, the reaction mixture was allowed to cool to rt, and di(1-adamantyl)-n-butylphosphine (18.2 mg, 0.0508 mmol), Pd(OAc)₂ (10.4 mg, 0.0462 mmol), and (R)-6-chloro-3-(3-methyl-2-oxopiperidin-3-yl)pyridin-2(1H)-one (133 mg, 0.554 mmol) were added to the vial under air. The vial was resealed, and its nitrogen atmosphere was reestablished via three evacuate and backfill cycles, taking care while the solvent bubbled. Degassed saturated aqueous solution of NaHCO₃ (1.4 mL, 1.4 mmol) was added through the septum, and the vial was heated in a 105° C. aluminum block for 16 h. Next, the mixture was diluted with pH 7 buffer and 1:9 EtOH/DCM and filtered over Celite®. The filtrate was diluted with brine, extracted with 1:9 EtOH/DCM, dried over Na₂SO₄, and concentrated. The residue was applied to a 5 g RediSep® silica pre-column using 1:19 EtOH/DCM and eluted through a 12 g RediSep® Rf Gold® silica column (gradient: 0 to 40% EtOH in DCM over 16 CVs followed by an isocratic elution of 40% EtOH in DCM) to afford a brown solid (25 mg). Further purification by preparative HPLC afforded Example 3 as its TFA salt (14.6 mg, 6.7%, yellow solid). ¹H NMR (400 MHz, CD₃OD) δ 1.46 (t, 3 H), 1.56-1.64 (m, 1 H), 1.66 (s, 3 H), 1.80-1.90 (m, 1 H), 1.97-2.12 (m, 1 H), 2.43 (td, 1 H), 3.32 (q, 2 H), 3.32-3.40 (m, 1 H), 3.54 (td, 1 H), 6.89 (d, 1 H), 7.71 (d, 1 H), 7.96 (dd, 1 H), 8.01 (s, 1 H), 8.25 (s, 1 H), 9.12-9.18 (m, 2 H). LCMS (ESI) m/z: 362.4 [M+H] (100%).

Example 4

(R)-6-(5-Chloroquinolin-7-yl)-3-(3-methyl-2-oxopiperidin-3-yl)pyridin-2(1H)-one; tautomer (R)-3-(6-(5-chloroquinolin-7-yl)-2-hydroxypyridin-3-yl)-3-methylpiperidin-2-one

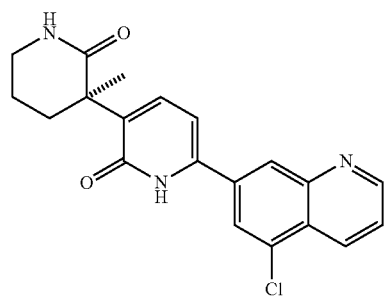 [SMILES: C[C@]1(c2ccc(-c3cc(Cl)c4cccnc4c3)[nH]c2=O)CCCNC1=O]

An oven-dried 2-5 mL microwave vial was charged with 7-bromo-5-chloroquinoline (100 mg, 0.412 mmol), potassium acetate (97.4 mg, 1.65 mmol, oven-dried), bis(neopentylglycolato)diboron (102 mg, 0.454 mmol), PdCl₂(dppf).CH₂Cl₂ (10.1 mg, 0.0124 mmol) and anhydrous 1,4-dioxane (2.0 mL). The mixture was sealed, sparged with nitrogen for ca. 7 min. through a septum, and heated in a 90° C. aluminum block for 2 h. After cooling to rt, (R)-6-chloro-3-(3-methyl-2-oxopiperidin-3-yl)pyridin-2(1H)-one (99.3 mg, 0.412 mmol), cesium fluoride (188 mg, 1.24 mmol), Pd(PPh₃)₄ (14.3 mg, 0.0124 mmol), and 1-butanol (1.0 mL)

were added. The reaction mixture was resealed and sparged with nitrogen for 5 min. Then, the reaction mixture was heated in a 100° C. aluminum block for 18 h. Upon cooling, the reaction mixture was partitioned between EtOAc and water. The aqueous layer was further extracted with 1:9 ethanol/DCM (2×). The combined organic layers were washed with brine, dried over MgSO$_4$, and concentrated. The residue was applied to a 5 g RediSep® pre-column using DCM and purified by MPLC using a 12 g RediSep® Rf Gold® main column (gradient: 0 to 20% EtOH in DCM) to afford Example 4 (45.0 mg, 30%) as a tan solid. LCMS (APCI) m/z: 368.3 [M+H] (100%). $^1$H NMR (400 MHz, CD$_3$OD) δ 1.52-1.61 (m, 1 H), 1.62 (s, 3 H), 1.75-1.87 (m, 1 H), 1.93-2.09 (m, 1 H), 2.41 (td, 1 H), 3.29-3.36 (m, 4 H), 3.50 (td, 1 H), 6.79 (d, 1 H), 7.65 (d, 1 H), 7.69 (dd, 1 H), 8.03 (d, 1 H), 8.27 (s, 1 H), 8.67 (d, 1 H), 8.98 (d, 1 H).

Further purification of a portion of Example 4 (40 mg) was accomplished by preparative HPLC, affording high purity Example 4 as a TFA salt (7.2 mg, 14% recovery). $^1$H NMR (400 MHz, CD$_3$OD) δ 1.55-1.64 (m, 1 H), 1.64 (s, 3 H), 1.79-1.89 (m, 1 H), 1.96-2.11 (m, 1 H), 2.42 (td, 1 H), 3.31-3.39 (m, 1 H), 3.53 (td, 1 H), 6.86 (d, 1 H), 7.69 (d, 1 H), 7.80 (dd, 1 H), 8.14 (d, 1 H), 8.32 (s, 1 H), 8.84 (d, 1 H), 9.06 (dd, 1 H). LCMS (ESI) m/z: 368.2 [M+H] (100%); $t_R$ (Method A)=2.01 min.

Example 5

(R)-6-(5-Cyclopropylquinolin-7-yl)-3-(3-methyl-2-oxopiperidin-3-yl)pyridin-2(1H)-one; tautomer (R)-3-(6-(5-cyclopropylquinolin-7-yl)-2-hydroxypyridin-3-yl)-3-methylpiperidin-2-one

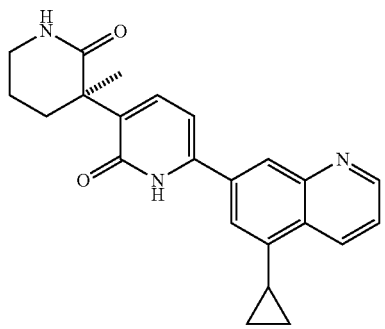 [SMILES: C[C@]1(c2ccc(-c3cc(C4CC4)c4cccnc4c3)[nH]c2=O)CCCNC1=O]

Example 5 was prepared in a similar manner to Example 3. Purification was accomplished by preparative HPLC, and Example 5 (21.5 mg, 13%) was isolated as its TFA salt. $^1$H NMR (400 MHz, CD$_3$OD) δ 0.95-1.01 (m, 2 H), 1.23-1.30 (m, 2 H), 1.55-1.64 (m, 1 H), 1.65 (s, 3 H), 1.80-1.90 (m, 1 H), 1.97-2.11 (m, 1 H), 2.43 (td, 1 H), 2.53-2.62 (m, 1 H), 3.32-3.40 (m, 1 H), 3.54 (td, 1 H), 6.85 (d, 1 H), 7.70 (d, 1 H), 7.81 (s, 1 H), 7.97 (dd, 1 H), 8.22 (s, 1 H), 9.14 (dd, 1 H), 9.41 (d, 1 H). LCMS (ESI) m/z: 374.3 [M+H] (100%); $t_R$ (Method C)=2.94 min. LCMS data were acquired immediately prior to HPLC purification.

Example 6

(R)-6-(5-Fluoroquinolin-7-yl)-3-(3-methyl-2-oxopiperidin-3-yl)pyridin-2(1H)-one; tautomer (R)-3-(6-(5-fluoroquinolin-7-yl)-2-hydroxypyridin-3-yl)-3-methylpiperidin-2-one

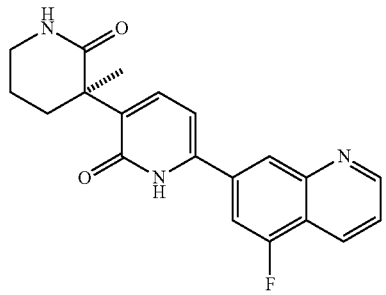 [SMILES: C[C@]1(c2ccc(-c3cc(F)c4cccnc4c3)[nH]c2=O)CCCNC1=O]

A 2-5 mL microwave vial was charged with a ca. 1:2 mixture of 7-chloro-5-fluoroquinoline and 5-chloro-7-fluoroquinoline (50 mg, 0.28 mmol), Pd$_2$(dba)$_3$ (12.6 mg, 0.0138 mmol), tricyclohexylphosphine (7.7 mg, 0.027 mmol), bis(pinacolato)diboron (90.9 mg, 0.358 mmol), and potassium acetate (81.1 mg, 0.826 mmol, oven-dried). The vial was sealed with a cap containing a septum, and a nitrogen atmosphere was established inside. 1,4-Dioxane (1.8 mL) was then added, and the vial was heated in a 90° C. aluminum block for 4 h. After cooling to rt, the reaction mixture was partitioned between EtOAc and water. The organic layer was separated, dried over Na$_2$SO$_4$, and evaporated to afford a mixture of 5-fluoro-7-(4,4,5,5-tetramethyl-1,3,2-dioxaborolan-2-yl)quinoline and 7-fluoro-5-(4,4,5,5-tetramethyl-1,3,2-dioxaborolan-2-yl)quinoline as a yellow oil, which was used in the next step without further purification.

A 2-5 mL microwave was charged with Pd(OAc)$_2$ (3.9 mg, 0.017 mmol), di(1-adamantyl)-n-butylphosphine (12.5 mg, 0.0350 mmol), and (R)-6-chloro-3-(3-methyl-2-oxopiperidin-3-yl)pyridin-2(1H)-one (67.4 mg, 0.280 mmol). The vial was then sealed, and its atmosphere was exchanged with nitrogen. To this mixture was added a solution of 5-fluoro-7-(4,4,5,5-tetramethyl-1,3,2-dioxaborolan-2-yl)quinoline (63.7 mg, 0.233 mmol) in DMF (1.1 mL) followed by a saturated aqueous solution of NaHCO$_3$ (1.2 mL). The resulting mixture was heated overnight in a 100° C. aluminum block. Upon cooling, the reaction mixture was diluted with pH 7 buffer (ca. 3 mL). After stirring for ca. 10 min., a precipitate was removed by filtration. The filtrate was then extracted with 1:9 EtOH/DCM (3×), and the combined organic layers were dried over Na$_2$SO$_4$ and concentrated to afford pinkish liquid. Initial purification was accomplished by MPLC using a 12 g RediSep® Rf Gold® silica column and a gradient elution of 0 to 30% EtOH in DCM over 15 CV. Appropriate fractions were combined and evaporated to afford a bright yellow solid (24 mg). Further purification, including separation of a minor isomer, was accomplished by preparative HPLC, affording Example 6 (16.5 mg, 17%) isolated as its TFA salt. LCMS (ESI) m/z: 352.1 [M+H] (100%); $t_R$ (Method A)=1.73 min.

Example 7

(R)-3-(3-Methyl-2-oxopyrrolidin-3-yl)-6-(5-methylquinolin-3-yl)pyridin-2(1H)-one; tautomer (R)-3-(2-hydroxy-6-(5-methylquinolin-3-yl)pyridin-3-yl)-3-methylpyrrolidin-2-one

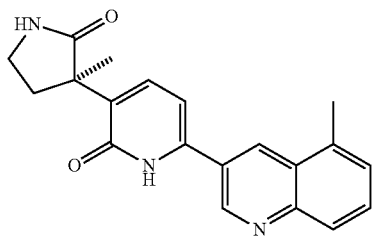 [SMILES: Cc1cccc2ncc(-c3ccc([C@@]4(C)CCNC4=O)c(=O)[nH]3)cc12]

Step 1: PdCl$_2$(dppf) (18 mg, 0.025 mmol) was added to a mixture of (R)-3-(6-chloro-2-methoxypyridin-3-yl)-3-methylpiperidin-2-one (60. mg, 0.25 mmol), 5-methyl-3-(4,4,5,5-tetramethyl-1,3,2-dioxaborolan-2-yl)quinoline (80.7 mg, 0.300 mmol), 2.0 M aqueous Na$_2$CO$_3$ (0.50 mL), and 1,4-dioxane (2.0 mL). The resulting mixture was stirred for 16 h at 110° C. The reaction mixture was then diluted with water and extracted with EtOAc (3×50 mL). The combined organic layers were dried over Na$_2$SO$_4$ and evaporated. The residue was purified by preparative TLC (developed with EtOAc) to afford (R)-3-(2-methoxy-6-(5-methylquinolin-3-yl)pyridin-3-yl)-3-methylpyrrolidin-2-one (86 mg, 99%) as a yellow solid. LCMS (ESI) m/z: 347.9 [M+H] (100%).

Step 2: A solution of (R)-3-(2-methoxy-6-(5-methylquinolin-3-yl)pyridin-3-yl)-3-methylpyrrolidin-2-one (86 mg, 0.25 mmol) in MeCN (2.0 mL) was treated with iodotrimethylsilane (0.50 mL) at 0° C. After stirring at rt for 16 h, the reaction mixture was concentrated, and the residue was purified by preparative HPLC (Column: Agela Durashell C18 250×21.2 mm*5 um; Mobile phase: from 5% MeCN (0.225% Formic acid) in water (0.225% Formic acid) to 25% MeCN (0.225% Formic acid) in water (0.225% Formic acid); Flow rate: 30 mL/min; Wavelength: 200 nm) to afford Example 7 (37 mg, 43%) as a formate salt. LCMS (ESI) m/z: 334.1 [M+H] (100%). $^1$H NMR (400 MHz, DMSO-d$_6$) δ 1.40 (s, 3 H), 1.83 (ddd, 1 H), 2.60-2.69 (m, 1 H), 2.75 (s, 3 H), 3.19-3.32 (m, 2 H), 6.86 (d, 1 H), 7.47-7.54 (m, 2 H), 7.61 (s, 1 H), 7.70 (dd, 1 H), 7.89 (d, 1 H), 8.80 (d, 1 H), 9.21 (d, 1 H), 12.11 (br. s., 1 H).

EP3 Radioligand SPA Binding Assay

To measure the ability of test compounds in the present invention to bind to the human EP3 receptor, and therefore have the potential to antagonize PGE2 activity, radioligand displacement assays were performed. Compound affinity was expressed as a K$_i$ value, defined as the concentration of compound required to decrease [$^3$H] PGE2 binding by 50% for a specific membrane batch at a given concentration of radioligand.

Test compounds were half log serially diluted in 100% DMSO (J. T. Baker #922401). 1 μL of each compound was added to appropriate wells of a 384-well plate (Matrix Cat #4322). Unlabeled PGE2 (Tocris Cat #2296) at a final concentration of 1 μM was used to determine non-specific binding. 1 μL of 100% DMSO (J. T. Baker #922401) was used to determine total binding. Millipore EP3 Chem1 membranes (prepared in-house from cell paste derived from the Millipore ChemiSCREEN™ Human Recombinant EP3 Prostanoid Receptor Calcium-Optimized Stable Cell Line (Millipore Cat # HTS092C, http://www.millipore.com/catalogue/item/hts092c)) were thawed and diluted in binding buffer (50 mM Hepes pH 7.4 (Lonza Cat #17-737), 5 mM MgCl$_2$ (Sigma-M1028), and 0.1% BSA (Sigma A-7409)) to a final concentration of 1 μg/25 μL. 25 μL of diluted membranes were added to prepared compound plates. WGA coated PVT SPA Beads (Perkin Elmer Cat # RPNQ0060) were diluted in binding buffer to a concentration of 4 μg/ul, and 25 μL of the SPA bead mixture was then added to each well for a final assay concentration of 100 μg/well. [$^3$H]-PGE2 (Perkin Elmer Cat #NET428) was diluted in binding buffer to a concentration of 3.375 pM, and 254 was added to all wells for a final assay concentration of 1.125 nM. Plates were incubated for 30 minutes at r.t. (approximately 25° C.) with shaking. Radioactivity associated with each well was measured after a 10 hour incubation using a Wallac Trilux MicroBeta plate-based scintillation counter and a normalized protocol at 1 minute read/well. The K$_d$ for [$^3$H]-PGE2 was determined by carrying out saturation binding, with data analysis by non-linear regression, fit to a one-site hyperbola (GraphPad Prism®). IC$_{50}$ determinations were made from competition curves, analyzed with a proprietary curve fitting program (SIGHTS), similar to GraphPad PRISM® and a 4-parameter logistic dose response equation. Ki values were calculated from IC$_{50}$ values, using the Cheng-Prusoff equation.

Table 5 below provides the Ki values of Examples for the binding affinity against human EP3 in accordance with the above-described assay. Results are reported as geometric mean Ki values, where the example is identified as a free base or designated salt that is made as a solution for the experiment and N is the number of samples tested for that example and is the sum of the forms identified with the corresponding number of the respective form in parentheses.

TABLE 5

BIOLOGICAL DATA

| Ex # | Human EP3 Ki [nM] | N |
|---|---|---|
| 1 (free base) | 3.3 | 10 |
| 2 (free base and TFA salt) | 7.2 | 8 (3/5) |
| 3 (TFA salt) | 4.6 | 1 |
| 4 (free base and TFA salt) | 8.9 | 7 (2/5) |
| 5 (TFA salt) | 7.3 | 1 |
| 6 (TFA salt) | 48.6 | 3 |
| 7 (formate salt) | 18.6 | 5 |

Assessment of Functional Activity

The functional activity of two Examples was determined by measuring the effect on cellular cAMP levels, under conditions whereby antagonism of the EP3 receptor could be measured. Compound activity was expressed as an IC$_{50}$ value, defined as the concentration of compound required to decrease agonist (sulprostone) activity by 50%. CHO-K1 cells expressing human prostaglandin E3 receptor (EP3, DiscoveRx #95-0159C2) were maintained in Ham's F-12 Nutrient Mixture (Invitrogen #11765-054) containing L-Glutamine (Gibco #25030-081), Geneticin (Gibco #10131-027), Pen Strep (Gibco #15070-063) and 10% heat-inactivated fetal bovine serum (Sigma #F4135). Cells were plated in 384-well Microtest Plates (Corning Life Sciences #353988) at 10,000 cells per well and maintained at 37°

Celsius in a humidified 5% $CO_2$ environment overnight. The following day, cells were washed twice with 50 μL of 1×HBSS (Hank's Balanced Salt Solution, Gibco #14025-092) and incubated in 10 μL of assay buffer (1×HBSS containing 20 mM HEPES pH 7.0 (4-(2-hydroxyethyl)-1-piperazineethanesulfonic acid, Gibco #15630-080), 0.1% BSA (bovine serum albumin, Sigma #A7409), and 500 μM 3-isobutyl-1-methylzanthin (IBMX, Sigma #15879)). Example compounds were half log serially diluted in 100% DMSO to generate an 11 point dose response, diluted in assay buffer, and 2 μL of each concentration was added to an assay-plate well. The final top concentration in the assay was 10 μM. After 20 minutes at r.t., 8 μL of assay buffer containing 100 μM forskolin (Tocris #1099) and 10 nM sulprostone (Tocris #3049) was added to each well and plates were held at r.t. for another 30 minutes. Cellular cAMP levels were determined using a Homogeneous Time-Resolved Fluorescence (HTRF) cAMP detection kit (cAMP HI-Range Assay Kit; CisBio #62AM6PEJ). The detection method is a competitive immunoassay between native cAMP produced by the cells and exogenous cAMP labeled with d2 dye. The tracer binding is visualized by a Mab anti-cAMP labeled with Cryptate. The specific signal (i.e. energy transfer) is inversely proportional to the concentration of cAMP in either standard or experimental sample. Detection solutions were prepared by adding 5 μL of labeled d2 cAMP and 5 of anti-cAMP antibody (both diluted 1:20 in cell lysis buffer; as provided and described in the cAMP detection kit protocol) to each well of the assay plate. The assay plates were then held at r.t. and after 60 minutes, changes in the HTRF signal were read with an Envision 2104 multi-label plate reader using excitation of 330 nm and emissions of 615 and 665 nm. Raw data were converted to nM cAMP by interpolation from a cAMP standard curve (as described in the cAMP detection kit protocol) and $IC_{50}$ determinations were made from the response curves analyzed with a curve fitting program, similar to GraphPad PRISM® and using a 4-parameter logistic dose response equation.

Table 6 below provides the $IC_{50}$ values of Examples 1 and 7 in accordance with the above-described assay. Results are reported as geometric mean $IC_{50}$ values, where the example is identified as a free base or designated salt that was made as a solution for the experiment and N is the number of samples tested for that example and is the sum of the forms identified with the corresponding number of the respective form in parentheses.

TABLE 6

| FUNCTIONAL $IC_{50}$ VALUES | | |
|---|---|---|
| Ex # | $IC_{50}$ [nM] | N |
| 1 (free base) | 30.8 | 2 |
| 7 (formate salt) | 34.1 | 1 |

Other features and advantages of this invention will be apparent from this specification and the claims which describe the invention. It is to be understood that both the detailed description is exemplary only and not restrictive of the invention as claimed.

All patents, patent applications and references referred to herein are hereby incorporated by reference in their entirety.

What is claimed is:

1. A compound of Formula I:

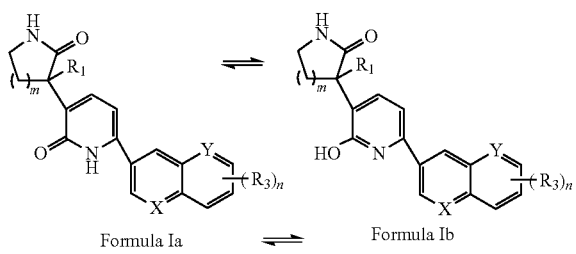

wherein
m is 1 or 2;
n is 0, 1, or 2;
X and Y are nitrogen or $CR^2$, provided that when X is nitrogen, Y is $CR^2$ and further provided that when X is $CR^2$, Y is nitrogen;
$R^1$ is H, $C_{1-6}$alkyl, or $C_{3-6}$cycloalkyl;
$R^2$ is H, halogen, $C_{1-6}$alkyl, or $C_{3-6}$cycloalkyl, wherein alkyl may be substituted with up to 3 halogens; and
Each $R^3$ is independently halogen, $C_{1-6}$alkyl, or $C_{3-6}$cycloalkyl, wherein alkyl may be substituted with up to 3 halogens; or a pharmaceutically acceptable salt thereof, or a solvate of said compound or salt thereof.

2. The compound of claim 1, wherein
m is 1 or 2;
n is 0;
X is nitrogen;
Y is $CR^2$;
$R^1$ is H, $C_{1-6}$alkyl, or $C_{3-6}$cycloalkyl; and
$R^2$ is F, Cl, $C_{1-3}$alkyl or cyclopropyl, wherein alkyl may be substituted with up to 3 halogens; or a pharmaceutically acceptable salt thereof, or a solvate of said compound or salt thereof.

3. The compound of claim 1, wherein
m is 1 or 2;
n is 0;
Y is nitrogen;
X is $CR^2$;
$R^1$ is H, $C_{1-6}$alkyl, or $C_{3-6}$cycloalkyl; and
$R^2$ is F, Cl, $C_{1-3}$alkyl or cyclopropyl, wherein alkyl may be substituted with up to 3 halogens; or a pharmaceutically acceptable salt thereof, or a solvate of said compound or salt thereof.

4. The compound of claim 1, wherein X, Y, $R^2$, and $R^3$ provide

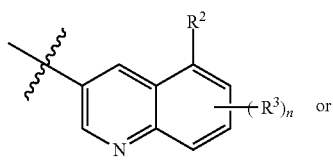 or

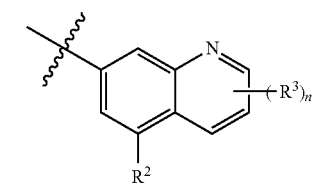

n is 0 or 1;

R² is F, Cl, methyl, ethyl, CFH₂, CF₂H, CF₂CH₃, CF₃, or cyclopropyl; and

R³ is F, Cl, methyl, ethyl, CFH₂, CF₂H, CF₂CH₃, CF₃, or cyclopropyl; or a pharmaceutically acceptable salt thereof, or a solvate of said compound or salt thereof.

5. The compound of claim 1, wherein X, Y, and R² provide

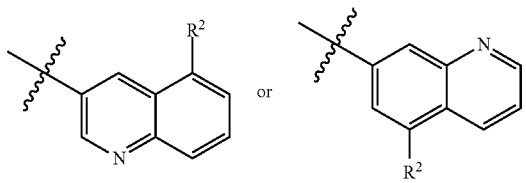

n is 0; and

R² is F, Cl, methyl, ethyl, CFH₂, CF₂H, CF₂CH₃, CF₃, or cyclopropyl; or a pharmaceutically acceptable salt thereof, or a solvate of said compound or salt thereof.

6. The compound of claim 1, wherein the compound is (R)-3-(3-Methyl-2-oxopiperidin-3-yl)-6-(5-methylquinolin-7-yl)pyridin-2(1H)-one or (R)-3-(2-hydroxy-6-(5-methylquinolin-7-yl)pyridin-3-yl)-3-methylpiperidin-2-one, or a pharmaceutically acceptable salt thereof, or a solvate of said compound or salt thereof.

7. The compound of claim 1, wherein the compound is (R)-6-(5-Ethylquinolin-7-yl)-3-(3-methyl-2-oxopiperidin-3-yl)pyridin-2(1H)-one or (R)-3-(6-(5-ethylquinolin-7-yl)-2-hydroxypyridin-3-yl)-3-methylpiperidin-2-one, or a pharmaceutically acceptable salt thereof, or a solvate of said compound or salt thereof.

8. The compound of claim 1, wherein the compound is (R)-6-(5-Chloroquinolin-7-yl)-3-(3-methyl-2-oxopiperidin-3-yl)pyridin-2(1H)-one or (R)-3-(6-(5-chloroquinolin-7-yl)-2-hydroxypyridin-3-yl)-3-methylpiperidin-2-one, or a pharmaceutically acceptable salt thereof, or a solvate of said compound or salt thereof.

9. The compound of claim 1, wherein the compound is (R)-6-(5-Cyclopropylquinolin-7-yl)-3-(3-methyl-2-oxopiperidin-3-yl)pyridin-2(1H)-one or (R)-3-(6-(5-cyclopropylquinolin-7-yl)-2-hydroxypyridin-3-yl)-3-methylpiperidin-2-one, or a pharmaceutically acceptable salt thereof, or a solvate of said compound or salt thereof.

10. The compound of claim 1, wherein the compound is (R)-6-(5-Fluoroquinolin-7-yl)-3-(3-methyl-2-oxopiperidin-3-yl)pyridin-2(1H)-one or (R)-3-(6-(5-fluoroquinolin-7-yl)-2-hydroxypyridin-3-yl)-3-methylpiperidin-2-one, or a pharmaceutically acceptable salt thereof, or a solvate of said compound or salt thereof.

11. The compound of claim 1, wherein the compound is (R)-3-(3-Methyl-2-oxopyrrolidin-3-yl)-6-(5-methylquinolin-3-yl)pyridin-2(1H)-one or (R)-3-(2-hydroxy-6-(5-methylquinolin-3-yl)pyridin-3-yl)-3-methylpyrrolidin-2-one, or a pharmaceutically acceptable salt thereof, or a solvate of said compound or salt thereof.

12. The compound of claim 1, wherein the compound is (R)-3-(3-Methyl-2-oxopiperidin-3-yl)-6-(5-methylquinolin-3-yl)pyridin-2(1H)-one or (R)-3-(2-hydroxy-6-(5-methylquinolin-3-yl)pyridin-3-yl)-3-methylpiperidin-2-one, or a pharmaceutically acceptable salt thereof, or a solvate of said compound or salt thereof.

13. The compound of claim 12, wherein the compound is the crystalline monohydrate, having characteristic peaks at Angle 2θ(°) values of about 9.5, 13.7, 19.2, 20.7, and 25.3.

14. The compound of claim 12, wherein the compound is the crystalline hydrochloride salt, having characteristic peaks at Angle 2θ(°) values of about 18.4, 20.0, 21.1, 22.8, and 27.7.

15. The compound of claim 1, wherein the compound is independently selected from any one of the following compounds or a pharmaceutically acceptable salt thereof, or solvate of said compound or salt thereof:

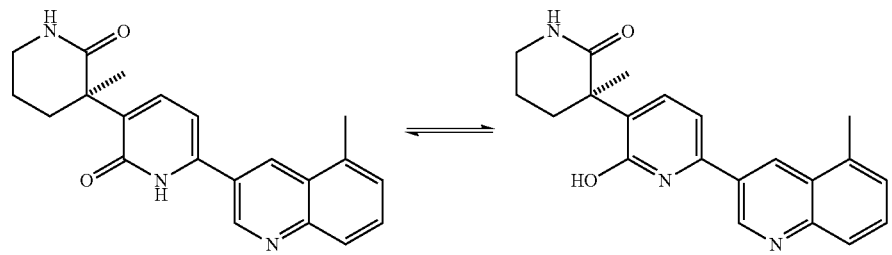

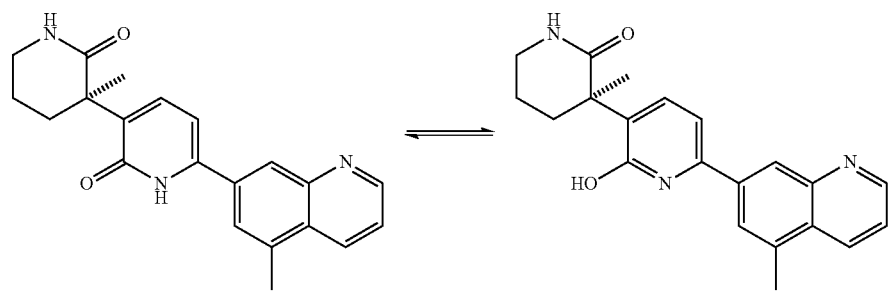

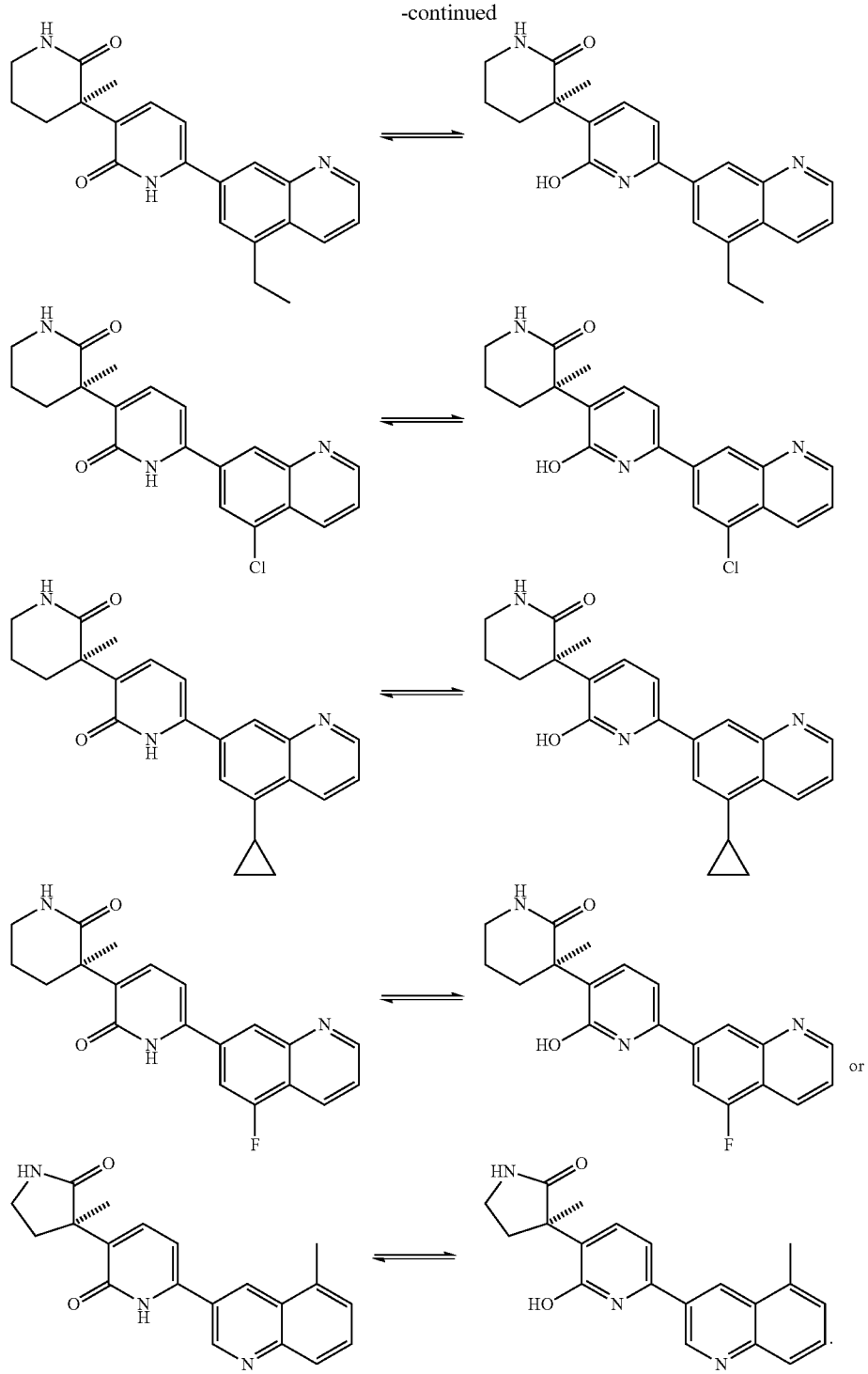
16. A pharmaceutical composition comprising the compound of Formula I of claim 1, or a pharmaceutically acceptable salt thereof, or solvate of said compound or salt thereof, and a pharmaceutically acceptable excipient.
* * * * *